United States Patent
Patscheider et al.

(10) Patent No.: US 12,259,599 B2
(45) Date of Patent: Mar. 25, 2025

(54) SHAPE CHANGING OPTICAL DEVICE FOR OPHTHALMIC TESTING DEVICES

(71) Applicant: OPTOTUNE AG, Dietikon (CH)

(72) Inventors: Roman Patscheider, Winterthur (CH); Manuel Aschwanden, Allenwinden (CH); David Andreas Niederer, Küttigen (CH); Chris Laning, Windisch (CH); Aaron Gerratt, Zürich (CH)

( * ) Notice: Subject to any disclaimer, the term of this patent is extended or adjusted under 35 U.S.C. 154(b) by 621 days.

(21) Appl. No.: 17/413,577

(22) PCT Filed: Dec. 16, 2019

(86) PCT No.: PCT/EP2019/085453
§ 371 (c)(1),
(2) Date: Jun. 14, 2021

(87) PCT Pub. No.: WO2020/120806
PCT Pub. Date: Jun. 18, 2020

(65) Prior Publication Data
US 2022/0066239 A1 Mar. 3, 2022

(30) Foreign Application Priority Data
Dec. 14, 2018 (EP) .................................... 18212803

(51) Int. Cl.
*G02B 3/14* (2006.01)
*G02B 26/00* (2006.01)
(Continued)

(52) U.S. Cl.
CPC ............... *G02C 7/085* (2013.01); *G02B 3/14* (2013.01); *G02B 26/004* (2013.01); *A61B 3/036* (2013.01); *A61B 3/1035* (2013.01)

(58) Field of Classification Search
CPC ........ G02C 7/085; G02B 3/14; G02B 26/004; G02B 7/00; A61B 3/028; A61B 3/036; A61B 3/103; A61B 3/1035
See application file for complete search history.

(56) References Cited

U.S. PATENT DOCUMENTS 4,226,507 A * 10/1980 Fuschetto .......... G02B 26/0825
359/849
5,108,429 A * 4/1992 Wiley ................... A61F 2/1635
623/6.22
(Continued)

FOREIGN PATENT DOCUMENTS

CN 103365027 10/2013
CN 105974499 9/2016
(Continued)

OTHER PUBLICATIONS

Yanwei Zhang et al., Thermally Actuated Microprobes for a New Wafer Probe Card, 8 IEEE Journal of Microelectromechanical Systems 43-49 (1999). (Year: 1999).*
(Continued)

*Primary Examiner* — Cara E Rakowski
*Assistant Examiner* — Wesley Scott Ashton
(74) *Attorney, Agent, or Firm* — JMB Davis Ben-David

(57) ABSTRACT

The present invention relates to An optical device (1), particularly for an ophthalmic device, comprising: a container (2) enclosing an internal space (3) of the container (2), wherein the internal space (3) is filled with a transparent liquid (L), and wherein the container (2) comprises a transparent bottom (21) and a transparent and elastically deformable membrane (22) opposing said bottom (21) such that the liquid (L) is arranged between the membrane (22) and the bottom (21), a deformable annular lens shaping element (4) connected to the membrane (22) so that a circumferential edge (41) of the lens shaping element (4) defines a central
(Continued)

area (23) of the membrane (22) so that light can pass through the container (2) via the central area (23) and the bottom (21), wherein in a non-deformed state said edge (41) lies in a plane, and an adjustable spherical power and an adjustable cylindrical power, wherein for adapting the cylindrical power of the optical device (1), the lens shaping element (4) is configured to be bent out of said plane (P).

18 Claims, 23 Drawing Sheets

(51) Int. Cl.
  *G02C 7/08* (2006.01)
  *A61B 3/036* (2006.01)
  *A61B 3/103* (2006.01)

(56) References Cited

U.S. PATENT DOCUMENTS

| | | | | |
|---|---|---|---|---|
| 5,171,266 | A * | 12/1992 | Wiley | G02B 3/14 623/6.22 |
| 5,203,788 | A * | 4/1993 | Wiley | G02B 3/14 623/6.22 |
| 5,371,629 | A | 12/1994 | Kurtin et al. | |
| 5,917,657 | A * | 6/1999 | Kaneko | H04N 13/236 348/E13.064 |
| 7,646,544 | B2 | 1/2010 | Batchko | H10N 30/2027 359/666 |
| 7,656,073 | B2 * | 2/2010 | Doshida | G02B 3/12 310/330 |
| 7,701,643 | B2 * | 4/2010 | Batchko | B33Y 50/02 359/665 |
| 8,072,689 | B2 * | 12/2011 | Bolis | G02B 26/0825 359/666 |
| 8,087,778 | B2 * | 1/2012 | Gupta | G02C 7/085 359/666 |
| 8,390,939 | B2 * | 3/2013 | Henriksen | G03B 3/10 359/694 |
| 8,542,445 | B2 * | 9/2013 | Bolis | G02B 3/14 359/666 |
| 8,638,502 | B2 * | 1/2014 | Pugh | G02B 3/14 351/159.68 |
| 8,699,141 | B2 * | 4/2014 | Aschwanden | G02B 7/10 359/666 |
| 8,755,124 | B2 * | 6/2014 | Aschwanden | G02B 26/004 359/666 |
| 9,158,127 | B2 * | 10/2015 | Pugh | A61F 2/1627 |
| 9,164,202 | B2 * | 10/2015 | Batchko | G02B 3/12 |
| 9,810,923 | B2 * | 11/2017 | Stevens | G02C 7/085 |
| 9,874,664 | B2 * | 1/2018 | Stevens | G02C 7/083 |
| 10,401,537 | B2 * | 9/2019 | Batchko | G02B 26/005 |
| 10,492,676 | B2 * | 12/2019 | Boutinon | A61B 3/0075 |
| 10,823,981 | B2 * | 11/2020 | Stevens | G02B 3/14 |
| 2007/0075922 | A1 * | 4/2007 | Jessop | G09G 3/348 345/49 |
| 2010/0182703 | A1 | 7/2010 | Bolis | |
| 2011/0032624 | A1 * | 2/2011 | Bolis | G02B 26/0825 359/666 |
| 2018/0335649 | A1 | 11/2018 | Tsai | |
| 2020/0363566 | A1 * | 11/2020 | Herbert | G02B 3/14 |
| 2021/0165207 | A1 * | 6/2021 | Peyman | G02B 3/14 |

FOREIGN PATENT DOCUMENTS

| | | | | |
|---|---|---|---|---|
| DE | 4217853 | A1 * | 12/1993 | A61B 3/028 |
| EP | 2869097 | A1 * | 5/2015 | G02B 26/0816 |
| JP | 1989166004 | | 6/1989 | |
| JP | 3206420 | | 9/2001 | |
| JP | 2010518444 | | 5/2010 | |
| WO | 2013143630 | | 10/2013 | |
| WO | 2013144533 | | 10/2013 | |
| WO | 2013144592 | | 10/2013 | |

OTHER PUBLICATIONS

Ruediger G. Ballas et al. The Constituent Equations of Pieoelectric Multilayer Bending Actuators in Closes Analytical Form and Experimental Results, Sensors and Actuators A 130-131 (2006) 91-98. (Year: 2006).*

Lens Form: Sphere, Cylinder, and Axis, 2010, pp. 1-8 [online], [retrieved Oct. 15, 2023], retrieved from the Internet <URL: https://www.laramyk.com/resources/education/lens-form-and-theory/lens-form-sphere-cylinder-and-axis/>. (Year: 2010).*

Jenean Carlton, Part 1: Understanding PRISM, 2012, pp. 1-8 [online], [retrieved Oct. 16, 2023], retrieved from the Internet <URL: https://www.eyecarebusiness.com/issues/2012/october-2012/part-1-understanding-prism>. (Year: 2012).*

Propylene Carbonate, 2017, pp. 1-2 [online], [retrieved Oct. 14, 2023], retrieved from the Internet <URL: http:/web.archive.org/web/20171014003942/https://www.chemicalbook.com/ProductChemicalPropertiesCB8852744_EN.htm>. (Year: 2017).*

Mark E. Wilkinson et al., Optics Review 1-121 (2017). (Year: 2017).*

Ananya Pritam Gogoi, Spare Parts Standardization and Its Impact on Purchasing Leverage, 2018, pp. 1-15 [online], [retrieved Oct. 17, 2023], retrieved from the Internet <URL: https://www.beroeinc.com/whitepaper/standardization-imapact-on-purchasing/#:~:text=Parts%20standardization%20across%20 . . . >. (Year: 2018).*

Tunable Lens Device, 2013, pp. 1-93 [online], [retrieved Jun. 8, 2024], retrieved from the Internet <URL: https://priorart.ip.com/IPCOM/000232447>. (Year: 2013).*

Nazmul Hasan et al., Larger Aperture Tunable-focus Liquid Lens Using Shape Memory Alloy Spring, 24 Optics Express 13334-13342 (2016). (Year: 2016).*

Point Contact, 2024, pp. 1-3 [online], [retrieved Jun. 7, 2024], retrieved from the Internet <URL: https://www.oed.com/dictionary/point-contact_n>. (Year: 2024).*

Matthias C. Wapler et al., A Compact, Larger-aperture Tunable Lens with Adaptive Spherical Correction, 2014, pp. 1-4 [online], [ retrieved Nov. 12, 2024], retrieved from the Internet <URL: https://arxiv.org/pdf/1411.3746>. (Year: 2014).*

I.S. Park et al., Multifunction Liquid Lens for High-performance Miniature Cameras, 2016, pp. 776-779 [online], [retrieved Nov. 12, 2024], retrieved from the Internet <URL: https://ieeexplore.ieee.org/stamp/stamp.jsp?tp=&arnumber=7421744>. (Year: 2016).*

* cited by examiner

SHAPE CHANGING OPTICAL DEVICE FOR OPHTHALMIC TESTING DEVICES

CROSS-REFERENCE TO RELATED APPLICATIONS

This is the U.S. National Stage of International Patent Application No. PCT/EP2019/085453 filed on Dec. 16, 2019, which in turn claims the benefit of European Patent Application No. 18212803.3 filed on Dec. 14, 2018.

FIELD OF THE INVENTION

The present invention relates to an optical device, particularly for an ophthalmic device.

BACKGROUND OF THE INVENTION

Ophthalmological test equipment must normally meet certain requirements, which are laid down in corresponding standards. Particularly, according to ISO 10341:2012 (E) the spherical, cylindrical and prismatic power as well as the corresponding axes need to be adjustable.

Particularly, the spherical power of an refractory head shall have a minimum measuring range from 0 D to +15 D in steps of 0.25 D and from 0 D to −15 D in steps of 0.25 D. Furthermore, the cylindrical (or astigmatic) power shall have a minimum measuring range from 0 D to 5 D in steps of 0.25 D in plus or minus cylinder form, and the prismatic power shall have a minimum measuring range from 0Δ to 10Δ in steps of 1Δ or continuously.

Further requirements relate to free aperture and interpupillary distance.

Furthermore, it is known in the state of the art that astigmatism and defocus wavefront correction via Zernike modes can be produced with fluidic lenses (i.e. *Appl Opt.* 2009; 48(19):3580-7, cf. also: Lin Pang, Uriel Levy, Kyle Campbell, Alex Groisman, and Yeshaiahu Fainman, "Set of two orthogonal adaptive cylindrical lenses in a monolith elastomer device," Opt. Express 13, 9003-9013 (2005); Randall Marks, David L. Mathine, Gholam Peyman, Jim Schwiegerling, and Nasser Peyghambarian, "Adjustable fluidic lenses for ophthalmic corrections," Opt. Lett. 34, 515-517 (2009); Randall Marks, David L. Mathine, Gholam Peyman, Jim Schwiegerling, and N. Peyghambarian, "Adjustable adaptive compact fluidic phoropter with no mechanical translation of lenses," Opt. Lett. 35, 739-741 (2010)).

BRIEF SUMMARY OF THE INVENTION

Based on the above, it is an objective of the present invention to provide an optical device that can particularly be used in ophthalmic testing devices and that comprises a relatively small installation space and allows to integrate the adjustable spherical and cylindrical power (and particularly also the prismatic power) in a single optical element.

This problem is solved by an optical device.

Preferred embodiments of these aspects of the present invention are stated in the corresponding sub claims and are also described below.

An optical device, particularly for an ophthalmic device, is disclosed, comprising:
a container enclosing an internal space of the container, wherein the internal space is filled with a transparent liquid, and wherein the container comprises a transparent bottom and a transparent and elastically deformable membrane opposing said bottom such that the liquid is arranged between the membrane and the bottom,
a deformable annular lens shaping element connected to the membrane so that a circumferential (e.g. circular) edge of the lens shaping element defines a central area of the membrane so that light can pass through the container via the central area and the bottom, wherein in a non-deformed state said edge of the lens shaping element defines a plane (i.e. a flat virtual surface),
and wherein the optical device comprises an adjustable spherical power, and an adjustable cylindrical power, wherein for adapting the cylindrical power of the optical device, the lens shaping element is configured to be bent out of said plane, particularly so that the edge lies on a curved surface.

Particularly, according to an embodiment, the deformable lens shaping element can be an elastically deformable lens shaping element (e.g. for providing a restoring force).

According to an embodiment, for adapting the cylindrical power of the optical device, the lens shaping element is configured to be bent out of said plane so that said edge of the lens shaping element coincides with a cylindrical surface.

Particularly, the edge of the lens shaping element defines a contact line at which the central area of the membrane protrudes from the lens shaping element. Thus, in case the lens shaping element is moved axially (i.e. along the optical axis, the spherical power of the optical device is changed since this movement changes the spherical component of a curvature of said area of the lens). Further, in case the lens shaping element is bent out of said plane, the area of the membrane develops a cylindrical curvature and a corresponding cylindrical power.

According to an embodiment of the present invention, the optical device also comprises an adjustable prismatic power. Furthermore, for adjusting the prismatic power, the lens shaping element is configured to be tilted with respect to the optical axis of the optical device. Due to such a tilting, the prismatic power of the optical device is adjusted, since the container can e.g. be formed into a prism (e.g. starting from a flat state).

According to an embodiment of the present invention, the bottom is connected to a circumferential lateral wall of the container. Particularly, the bottom can be formed as a flat transparent plate (e.g. out of a glass or a polymer).

Further, according to an embodiment of the present invention, the lateral wall is integrally formed with the bottom. Particularly, the lateral wall and the bottom may be formed by a plate member comprising a recess for forming the internal space of the container or a part of this internal space.

Further, according to an embodiment of the present invention, the lateral wall and the bottom are separate elements that are connected to one another (e.g. glued to one another)

Further, according to an embodiment of the present invention, the membrane is connected to the lateral wall (e.g. glued to the lateral wall).

Further, according to an embodiment of the present invention, the container comprises a separate circumferential and flexible sealing element connecting the lens shaping element to the lateral wall or to the bottom.

Further, according to an embodiment of the present invention, the bottom forms an elastically deformable further membrane, and wherein the optical device comprises an annular further lens shaping element connected to the further membrane so that a circumferential (e.g. circular) edge of the further lens shaping element defines a central area of the further membrane so that light can pass the container through said central areas of the opposing membranes. Particularly, the lateral wall may form the annular further lens shaping element.

Further, according to an embodiment of the present invention, the further lens shaping element is a deformable further lens shaping element, wherein in a non-deformed state the edge of the further lens shaping element defines a further plane, wherein for adapting the cylindrical power of the optical device, also the further lens shaping element is configured to be bent out of said further plane, particularly so that said edge of the further lens shaping element lies on a curved surface and/or coincides with a cylindrical surface.

Further, according to an embodiment of the present invention, the further lens shaping element is rigid (particularly compared to the deformable lens shaping element).

Further, according to an embodiment of the present invention, the membrane forms a shell. i.e. is can be elastically bent out of its extension plane and generates restoring forces that try to bend the shell back to its initial flat state. Particularly, in the framework of the present invention, an elastically deformable membrane is considered to be a shell in case its nondimensional tension parameter k is smaller than 5. The nondimensional tension parameter k is defined as $$k = \sqrt{\frac{N_0 a^2}{D}}$$

where $N_0$ is the initial in plane radial tension load, a is the radius of the circular membrane or shell and D is the bending stiffness. It is defined as $$D = \frac{Eh^3}{12(1-v^2)}$$

where E is the modulus of elasticity, h is the membrane or shell thickness and v is the Poisson's ratio (cf. Sheploak, M., & Dugundji, J. (1998). Large deflections of clamped circular plates under initial tension and transitions to membrane behavior. Journal of Applied Mechanics, 65 (1), 107-115)

According to a further embodiment of the optical device according to the present invention, the optical device comprises a transparent optical element arranged between the membrane and the bottom such that the internal space of the container is divided into two separate regions, wherein each region is filled with the liquid, and wherein the optical device comprises a flexible first lateral wall (e.g. a bellows) and a flexible second lateral wall (e.g. a bellows), wherein the first lateral wall connects the lens shaping element to the optical element, and wherein the second lateral wall connects the optical element to the bottom. This allows to tilt and/or move the bottom by a separate actuator to adjust the prismatic and/or spherical power.

Further, according to an embodiment of the present invention, the optical device comprises an actuator system that is configured to bend the deformable lens shaping element out of the plane in order to adapt the cylindrical power.

Further, according to an embodiment of the present invention, the actuator system is configured to displace a plurality of points of the lens shaping element along an optical axis of the optical device to bend the deformable lens shaping element out of the plane in order to adapt the cylindrical power.

Further, according to an embodiment of the present invention, said points are arranged along the periphery of the lens shaping element. Particularly said points are arranged on a surface of the lens shaping element, wherein this surfaces faces away from the membrane. Particularly, the points can be arranged on a center line of the surface of the lens shaping element.

Further, according to an embodiment of the present invention, said plurality of points comprises at least five points, particularly six points. Particularly said plurality of points can be formed by exactly six points according to an embodiment.

Further, according to an embodiment of the present invention, the points are equidistantly spaced along the periphery of the lens shaping element.

Further, according to an embodiment of the present invention, the actuator system is configured to displace the points along the longitudinal axis by the same amount to adjust the spherical power of the optical device.

Further, according to an embodiment of the present invention, the actuator system comprises a pump configured to pump liquid into the internal space or out of the internal space to adjust the spherical power of the optical device.

Further, according to an embodiment of the present invention, the actuator system is configured to displace points of the lens shaping element such that the lens shaping element is tilted with respect to the optical axis of the optical device to adjust the prismatic power of the optical device.

Further, according to an embodiment of the present invention, the actuator system is configured to tilt the lens shaping elements with respect to one another to adjust the prismatic power of the optical device.

Particularly, according to a preferred embodiment of the present invention, the actuator system comprises a plurality of actuators, wherein each actuator is configured to displace one of the points.

Particularly, in an embodiment, each actuator comprises a mover that is movable back and forth along the optical axis of the optical device by means of the actuator, wherein each mover is coupled to the associated point of the lens shaping element, particularly through a compliant coupling element. In an embodiment, the respective actuator can be a linear push pull actuator.

Furthermore, according to a further embodiment, each actuator comprises a mover that is movable towards the lens shaping element along the optical axis of the optical device by means of the actuator, wherein each mover is configured to push against the associated point of the lens shaping element, particularly via a point contact, and wherein each actuator comprises a spring element configured to exert a restoring force on the associated point of the lens shaping element. Alternatively (or in addition), the respective actuator may also pull on the respective point of the lens shaping element.

Furthermore, according to an embodiment, the respective mover is formed by a permanent magnet or comprises a permanent magnet, and wherein the respective actuator comprises an electromagnet for moving the permanent magnet (mover) of the respective actuator.

According to an embodiment, the respective spring element is supported on the bottom. Alternatively, the respective spring element can be supported on the lateral wall.

Furthermore, according to an embodiment, the respective spring element can e.g. be a coil spring or a leaf spring (other spring elements are also possible).

Further, in an embodiment, the respective spring element is arranged in the internal space and immersed in the transparent liquid.

Alternatively, the respective spring element can be arranged outside the internal space of the container. In the latter case, the respective spring element can be integrally formed with the lens shaping element according to an embodiment of the present invention.

Furthermore, according to an embodiment, instead of multiple actuators for exerting forces on multiple points of the lens shaping element, the actuator system can comprise a bending actuator (such as an isomorph or an bimorph actuator). Particularly, in an embodiment, the bending actuator comprises at least a first annular active layer, wherein said first active layer is comprised by the lens shaping element (or even forms the lens shaping element), and wherein the first active layer is configured to (e.g. anisotropically) expand or contract in a first direction to bend the lens shaping element out of said plane so that the optical device comprises a cylindrical power with respect to a cylinder reference axis.

Furthermore, the bending actuator may comprise a second active layer that is comprised by the lens shaping element and configured to (e.g. anisotropically) expand or contract in a second direction (the second direction can be orthogonal to the first direction) to bend the lens shaping element out of said plane so that the optical device comprises the cylindrical power with respect to the cylinder reference axis. Particularly, the second active layer can be connected to the first active layer. Alternatively, the second direction can also be collinear to the first direction, wherein here, the second active layer preferably contracts when the first active layer expands and vice versa.

Furthermore, the bending actuator can comprise an annular passive layer comprised by the lens shaping element, wherein the passive layer can be connected to the first active layer (i.e. the bending actuator comprises an active layer and a passive layer) or wherein the passive layer is arranged between the first and the second active layer and connected to these active layers. Here, the bending actuator comprises three layers, i.e. the passive layer arranged between the first and the second active layer.

Particularly, the passive layer can comprise one of the following materials or is formed out of one of the following materials: steel, stainless steel, aluminum, an alloy comprising copper, brass, a polymer, PET, PMMA, a fibre-reinforced material, a carbon fiber reinforced polymer or other suitable materials.

Furthermore, particularly, the first and/or the second active layer comprises one of the following materials or is formed out of one of the following materials: a piezoelectric material, (Pb (Zr,Ti)O3 (PZT), Pb(Zn⅓Nb⅔)O3-PbTiO3 (PZN-PT)

Particularly, using a single bending (e.g. bimorph) actuator might only allow to tune the cylindrical power of one given cylinder reference axis. In order to be able to adjust orientation of the cylinder reference axis, two such deformable lens shaping elements can be used, whose cylinder reference axis are rotated by 45° with respect to each other.

Thus, according to a further embodiment, the actuator system comprises a further bending actuator that can be designed as the bending actuator described above to generate a cylindrical power with respect to a further cylinder reference axis, wherein the further cylinder axis is preferably rotated about 45° with respect to the cylinder reference axis of the other bending actuator (see above)

In case the respective active layer of the respective bending actuator is a piezoelectric material, the active layer is deformed (e.g. expanded or contracted) by applying an electrical field across the piezoelectric material (e.g. by means of a voltage difference between electrodes contacting the material)

Furthermore, according to an alternative embodiment, the actuator system comprises an actuator comprising at least a first annular active layer, wherein said first active layer is comprised by the lens shaping element (or forms the lens shaping element), wherein the first active layer comprises segments arranged side by side in a circumferential direction of the active layer that are configured to be selectively activated to contract or expand (e.g. isotropically or anisotropically). Also here, the bending actuator can comprise a second active layer (e.g. configured like the first active layer) connected to the first active layer or a passive layer connected to the first active layer. Further, the active layer may comprise a passive layer arranged between a first and a second active layer (see also above).

Particularly, the first (or the second) active layer may comprise twelve segments, wherein each segment comprises a length in the circumferential direction that corresponds to a center angle of the annular active layer of 30°.

Particularly, the passive layer of the bending actuator can comprise one of the materials stated above with regard to the passive layer or can be formed out of one of these materials.

Particularly, the segments of the first (or the second) active layer of the bending actuator can comprise one of the materials or can be formed out of one of the materials stated above with respect to the active layers.

Furthermore, the respective segment can be deformed (expanded or contracted) by applying an electrical field across the respective segment/piezoelectric material (e.g. by means of a voltage difference between electrodes contacting the respective segment)

Furthermore, according to an embodiment, the lens shaping element is elastically mounted to a holding structure of the optical device.

Particularly, in an embodiment, the actuator system is configured to tilt the bottom with respect to the lens shaping element to adjust the prismatic power of the optical device.

Furthermore, in an embodiment, the actuator system is configured to move the bottom along an optical axis of the optical device with respect to the lens shaping element to adjust the spherical power of the optical device.

Regarding the embodiments stated above certain actuators have been described that can be used to adjust the cylindrical and/or the spherical and/or the prismatic power of the optical device.

However, also other actuators that allow to displace a point of a lens shaping element or that allow to tilt or axially move a lens shaping element or another element of the optical device such as the bottom, can be used in the framework of the present invention.

Particularly, the actuator system can comprise one of the following actuators (e.g. for adjusting the cylindrical and/or spherical and/or prismatic power of the optical device)

- an electromagnet attracting or repelling a permanent magnet (see also above),
- a reluctance force actuator,
- a voice coil actuator,
- a rotary actuator (e.g. DC, brushless DC, stepper, ultrasonic motor, etc.), particularly comprising a mechanical transmission to convert a rotational motion to a linear motion (e.g. screw type, ballscrew, cam, wormgear, slider-crank mechanism, etc.), a piezo-stack (optionally with a stroke amplification mechanism),
a bending piezo (see also above),
a linear ultrasonic motor,
a shape memory alloy actuator,
a thermal expansion actuator, and
a hydraulic actuation system.

Furthermore, the optical device may comprise a control unit according to an embodiment that is configured to control the actuator system of the optical device so as to adjust the cylindrical power and/or the spherical power and/or the prismatic power of the optical device to a desired value, respectively.

Particularly, for conducting said adjustment, the control unit is configured to use a feedback signal. Particularly, the actuator system itself can be configured to provide this feedback signal. Particularly, the feedback signal can be indicative of a position of the respective actuator (e.g. servo actuator). Alternatively, or in addition, the optical device may comprise at least one sensor configured to provide a feedback signal that is indicative of a state (particularly a shape and/or curvature) of the lens shaping element (and/or of the further lens shaping element) so that the lens shaping element (and/or further lens shaping element) can e.g. be bent in a way that the optical device comprises a desired cylindrical power.

According to a further aspect of the present invention, an optical device, particularly for an ophthalmic device, is disclosed, comprising:
a container enclosing an internal space of the container, wherein the internal space is filled with a transparent liquid, and wherein the container comprises a transparent bottom and a transparent and elastically deformable membrane opposing said bottom such that the liquid is arranged between the membrane and the bottom,
a deformable annular lens shaping element connected to the membrane so that a circumferential edge of the lens shaping element defines a central area of the membrane so that light can pass through the container via the central area and the bottom, wherein in a non-deformed state said edge lies in a plane, and
an adjustable spherical power and an adjustable cylindrical power, wherein for adapting the cylindrical power of the optical device, the lens shaping element is configured to be deformed such that the shape of said edge is adjustable (e.g. between a circular shape and an elliptical shape) but still lies in said plane.

Here, the spherical and/or prismatic power can be adjusted by moving (spherical power) and tilting (prismatic power) the bottom with respect to the lens shaping element.

BRIEF DESCRIPTION OF THE DRAWINGS

In the following, further advantages, features as well as embodiments of the present invention are described with reference to the Figures, wherein.

DETAILED DESCRIPTION OF THE INVENTION

Figure 1:
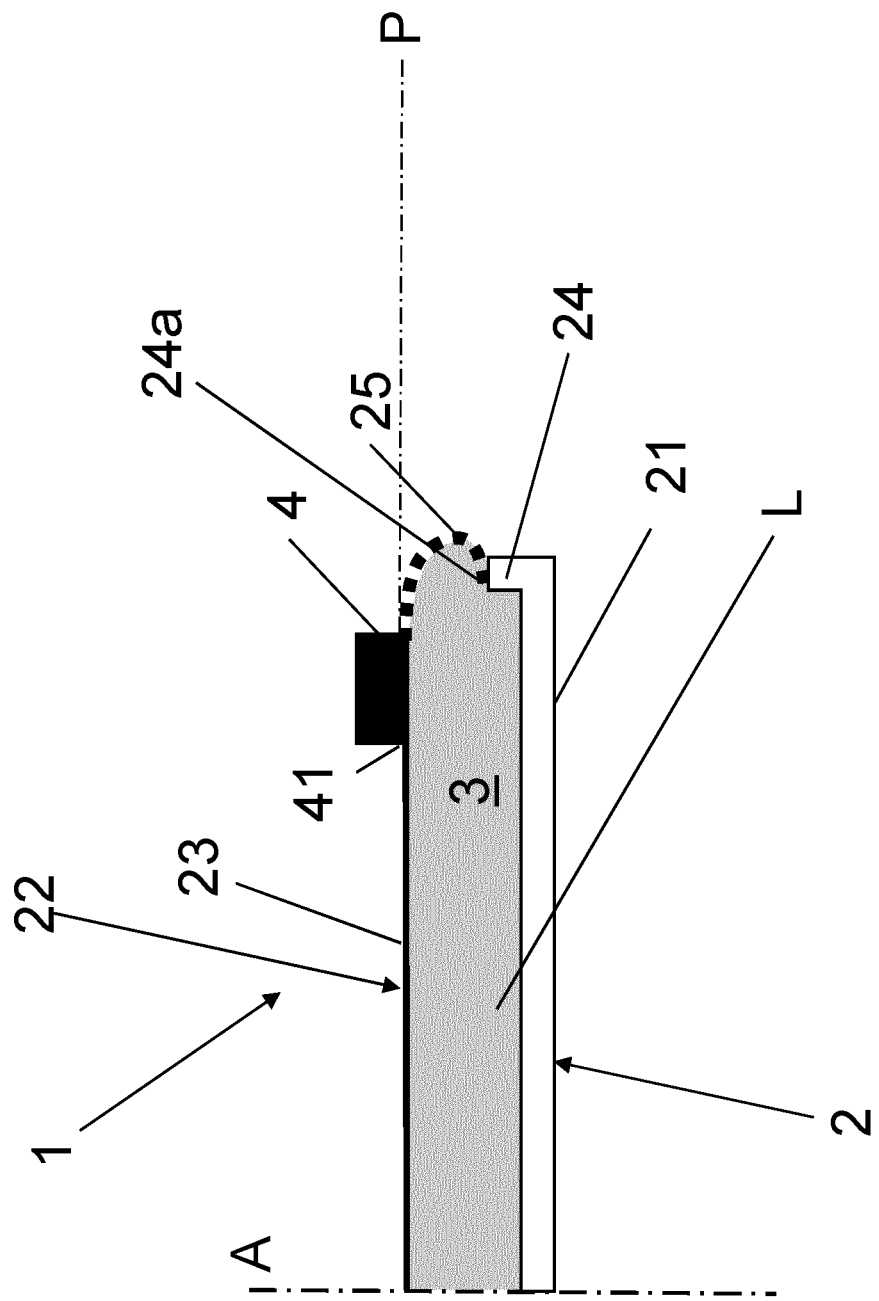
FIG. 1 shows a schematical cross sectional view of an embodiment of an optical device according to the present invention.

FIG. 1 shows an embodiment of an optical device 1 according to the present invention that is suitable for use in an ophthalmic (testing) device. Particularly, the optical device 1 comprises a container 2 enclosing an internal space 3 of the container 2 that is filled with a transparent liquid L. The container 2 further comprises a transparent bottom 21 and a transparent and elastically deformable membrane 22 opposing said bottom 21 such that the liquid L is arranged between the membrane 22 and the bottom 21.

Figure 2:
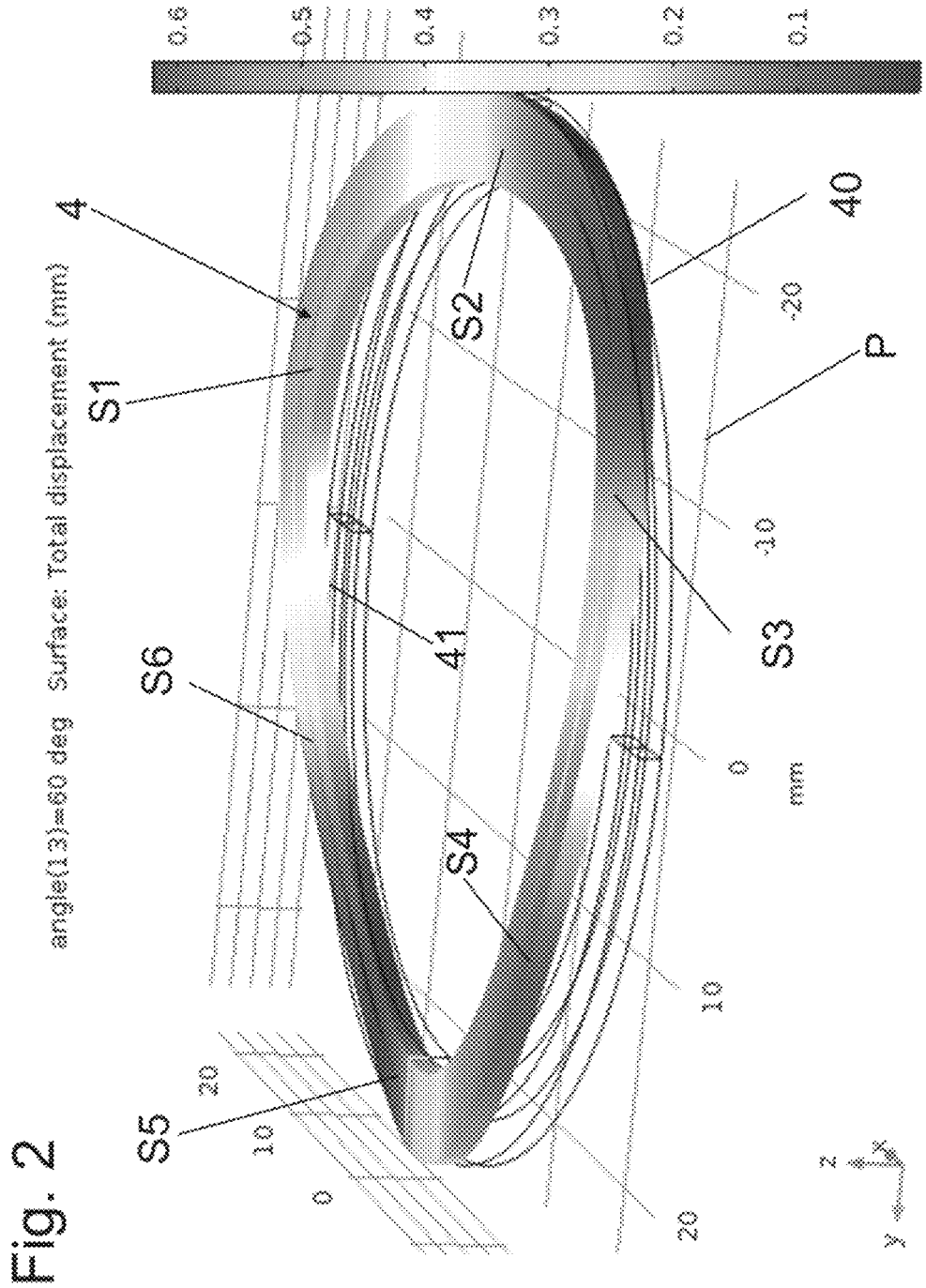
FIG. 2 shows the lens shaping element of an optical device according to the present invention in a state in which it is bent out of its extension plane to adjust the cylindrical power of the optical device.

Furthermore, the optical device 1 comprises a deformable annular lens shaping element 4 connected to the membrane 22 so that the lens shaping element 4, particularly a circumferential edge 41 thereof, defines a central area 23 of the membrane 22 so that light can pass through the container 2 via the central area 23 and the bottom 21, wherein in a non-deformed state the lens shaping element 4 defines a (virtual) plane, and wherein the optical device 1 comprises an adjustable spherical power, an adjustable prismatic power and an adjustable cylindrical power, wherein for adapting the cylindrical power of the optical device 1, the lens shaping element 4 is configured to be bent out of said plane P (cf. FIG. 2) so that the lens shaping element 4 defines a (virtual) cylindrical surface.

Particularly, when the lens shaping element 4 is axially moved (i.e. along the optical axis A), tilted with respect to said optical axis A (or with respect to the bottom 21), or bent out of the plane, the curvature of the central area 23 gets deformed accordingly, which allows to adjust the spherical power (movement of the lens shaping element 4 along the optical axis A), the prismatic power (tilt of the lens shaping element 4) and the cylindrical power (bending of lens shaping element 4 out of its initial plane P), which gives the area 23 a cylindrical curvature/component.

Figure 3:
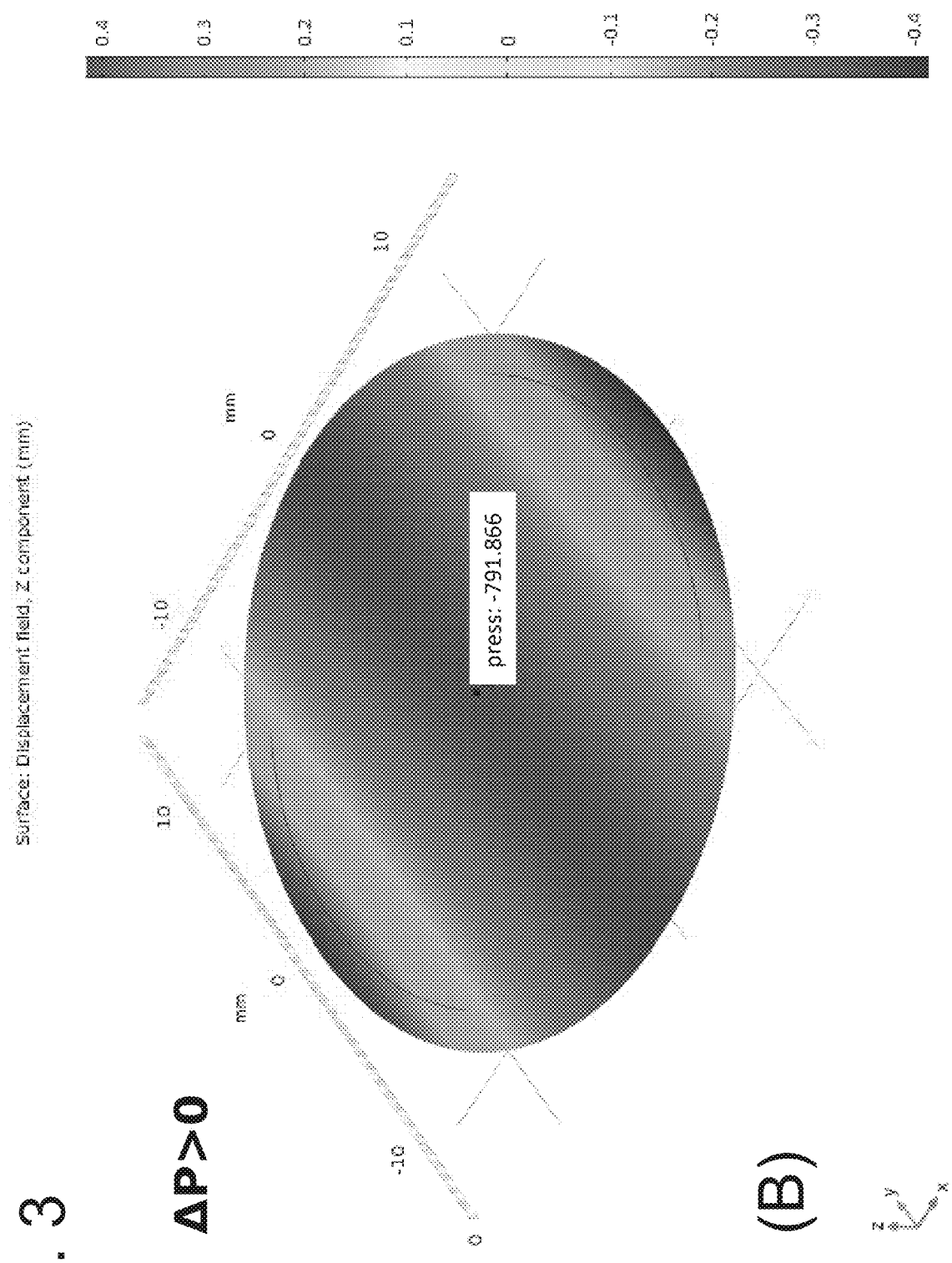
FIG. 3 with no pressure differential across the membrane of the optical device, its shape closely resembles the $Z_1^{-1}$ Zernike function. In order to achieve a purely cylindrical shape (zero optical power in the reference axis), the spherical component can be generated by increasing/decreasing the pressure in the container of the optical device, wherein (A) shows $\Delta p=0$ and (B) shows $\Delta p>0$.
Figure 4:
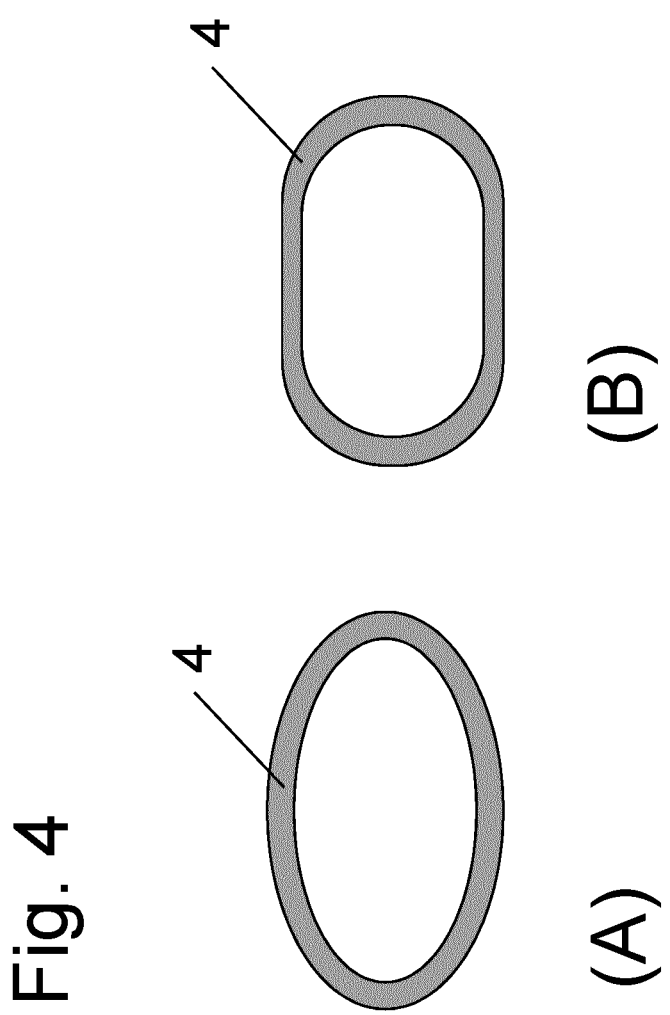
FIGS. 4 (A)-4 (B) show a further possibility for adjusting the cylindrical power.

Particularly, with no pressure differential across the membrane 22 of the optical device 1, its shape closely resembles the $Z_1^{-1}$ Zernike function. In order to achieve a purely cylindrical shape (zero power in the reference axis), the spherical component can be generated by increasing/decreasing the pressure of the liquid L in the container 2 of the optical device 1 with respect to the ambient pressure, wherein FIG. 3 (A) shows Δp=0 and FIG. 3 (B) shows Δp>0;

Alternatively, as shown in FIG. 4, the astigmatic (cylindrical) power can also be controlled by deforming the lens shaping element 4 in the (initial) membrane plane, e.g. by means of in-plane deformation of the lens shaping element's 4 aperture into a non-circular shape (like an ellipse/rounded rectangle) as shown in FIGS. 4 (A) and (B). Here, the ideal shape can be determined by minimizing the deviation from the desired wavefront.

In this case, the astigmatic ($Z_2^{-2}$) and spherical ($Z_2^0$) power of the lens/optical device 1 are linked by a fixed relation. (e.g. 0 cylindrical power at 0 spherical power) An additional spherically tunable element would be required to achieve all the necessary degrees of freedom.

Furthermore, as indicated in FIG. 1, the bottom 21 of the container 2 is connected (e.g. integrally) to a circumferential lateral wall 24 of the container 2, which lateral wall 24 comprises a face side 24a to which a flexible sealing element 25 can be connected (e.g. glued) that connects the lateral wall 24 to the lens shaping element 4.

In the embodiment shown in FIG. 1, the spherical power of the optical device 1 can be adjusted by moving the lens shaping element 4 along the optical axis A to increase the pressure in the internal space 3 of the container 2 and therewith a spherical curvature of the area 23 of the membrane 22 or to decrease the pressure in the internal space 3 and therewith the spherical curvature of the area 23.

Figure 5:
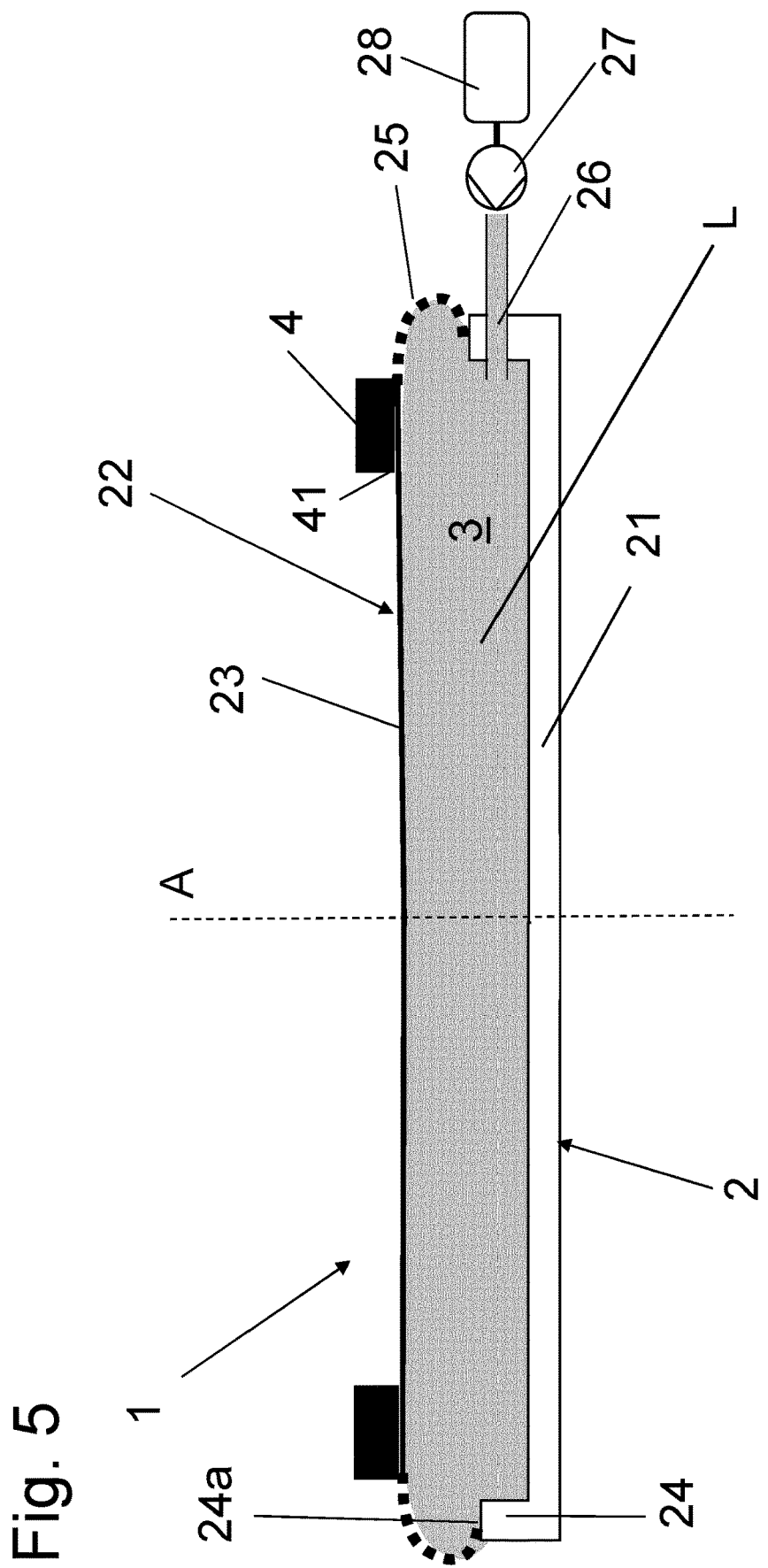
FIG. 5 shows a schematical cross sectional view of a further embodiment of an optical device according to the present invention, wherein here the container comprises an inlet for pumping liquid into and out of the internal space of the container of the optical device.

Alternatively, or in addition, the pressure in the container 2 may be adjusted according to FIG. 5 by pumping liquid L with a pump 27 from a reservoir 28 through an inlet 26 into the internal space 3 of the container 2, or by pumping liquid L from the internal space 3 into the reservoir 28.

Figure 6:
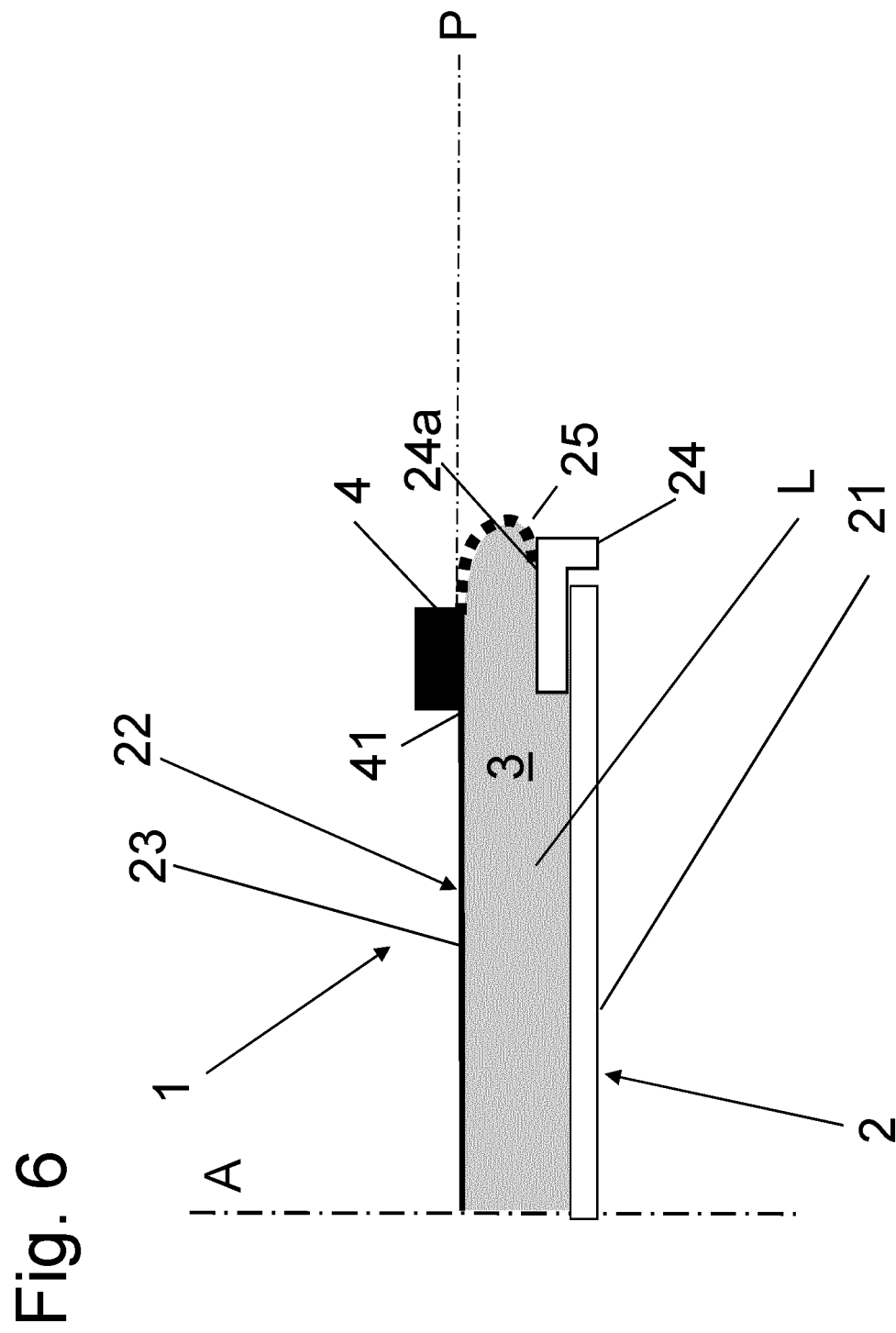
FIG. 6 shows a schematical cross sectional view of a modification of the embodiment shown in FIG. 1, wherein here the lateral wall and the bottom of the container are formed by separate elements connected to one another.

FIG. 6 shows a modification of the embodiment shown in FIG. 1, wherein here the lateral wall 24 forms a separate element with respect to the transparent bottom 21 that is connected, particularly glued, to the lateral wall 24.

Figure 7:
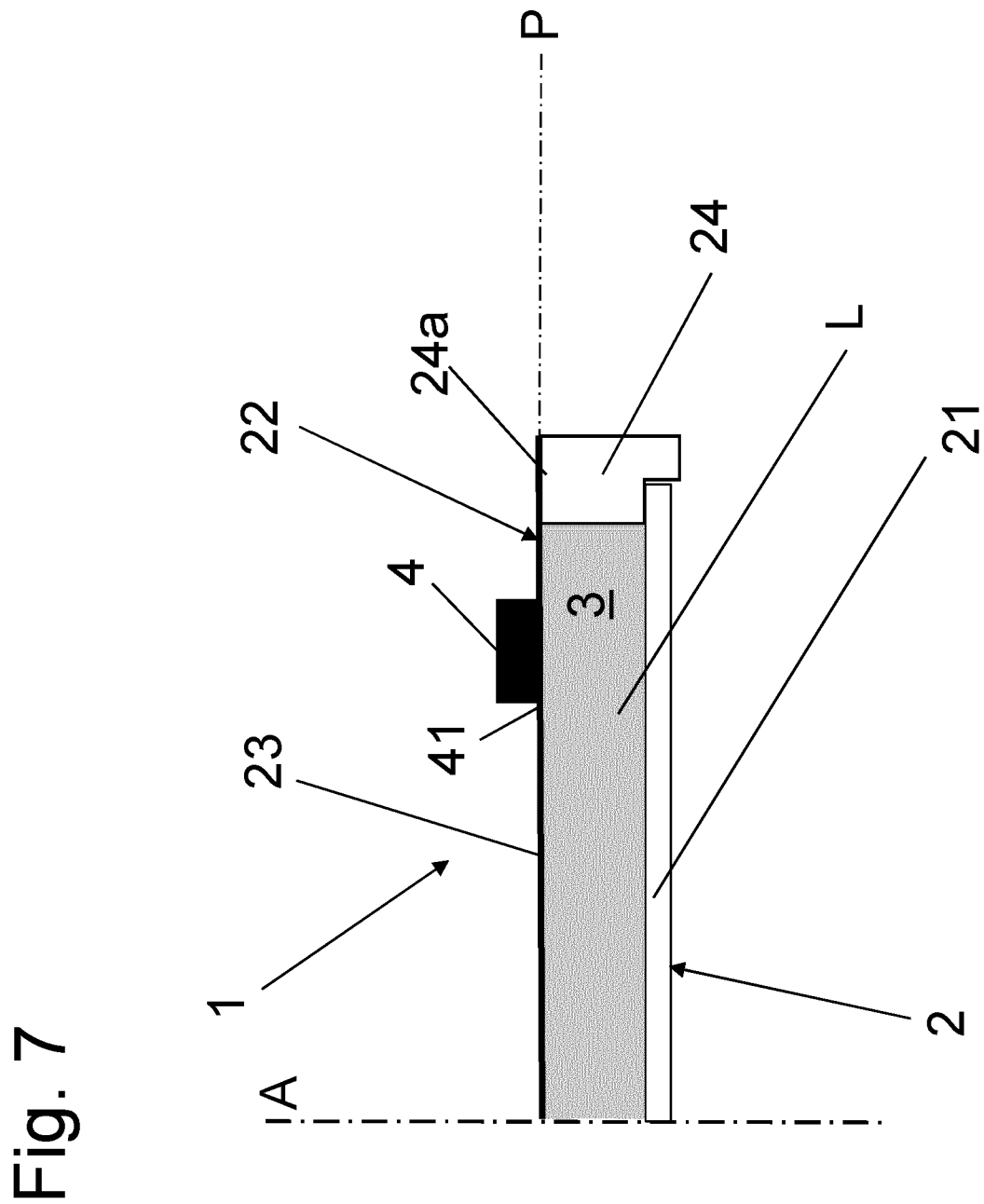
FIG. 7 shows a schematical cross sectional view of a modification of the embodiment shown in FIG. 6, wherein here the membrane is connected to the lateral wall to omit a separate sealing element connecting the lens shaping element to the lateral wall of the container.

Further, FIG. 7 shows a configuration in which the separate sealing element 25 shown in FIGS. 1, 5 and 6 is omitted. Instead, the membrane 22 connects to the face side 24a of the lateral wall 24 and thus comprises the sealing element as an integral portion.

Figure 8:
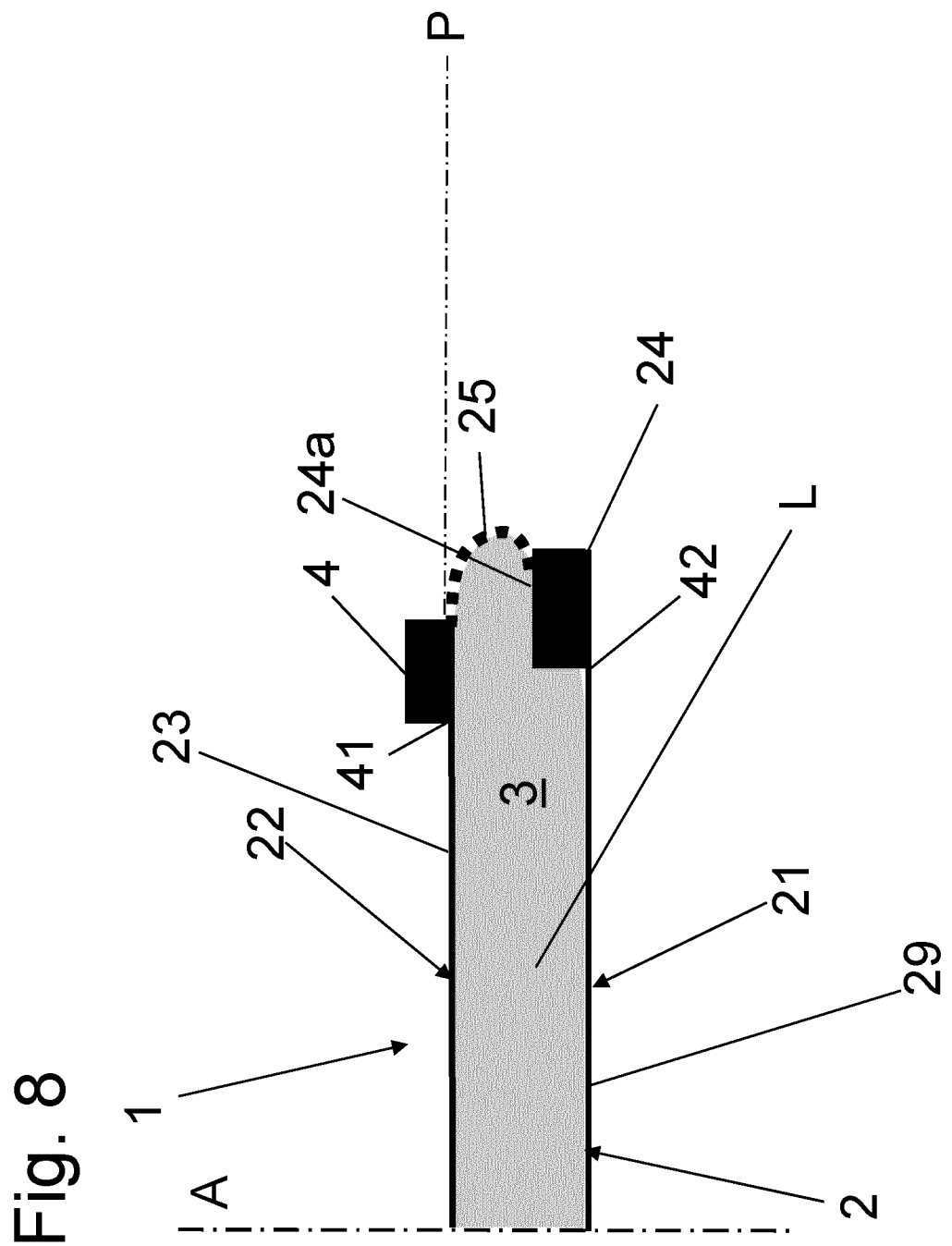
FIG. 8 shows a schematical cross sectional view of a further embodiment of an optical device according to the present invention, wherein here the container comprises two opposing membranes, a deformable lens shaping element, and a rigid lens shaping element.

FIG. 8 shows yet another embodiment of an optical device 1 according to the present invention, wherein here the rigid bottom 21 of the container 2 shown in the embodiments described above is replaced by a bottom in form of a transparent and elastically deformable further membrane 21, that connects to the lateral wall 24 which in this case forms a rigid further lens shaping element 24, which defines a central area 29 of the further membrane 21.

Particularly, in this dual surface embodiment, the further fixed and rigid lens shaping element 24 preferably comprises the same clear aperture as the deformable lens shaping element 4.

Here, particularly, the spherical power (combined effect of both membrane areas 23, 29), can be dominated by one of the membranes 22, 21 (if stiffnesses differ significantly) and can be controlled by changing the liquid pressure, e.g. by axial movement of one or both lens shaping elements 4, 24 (or by means of a pump 27 as shown in FIG. 5).

Furthermore, prismatic power can be controlled by tilting the lens shaping elements 4, 24 with respect to each other, while the cylindrical power can be controlled by out of plane bending of the deformable lens shaping element 4 which will be described in more detail below.

Figure 9:
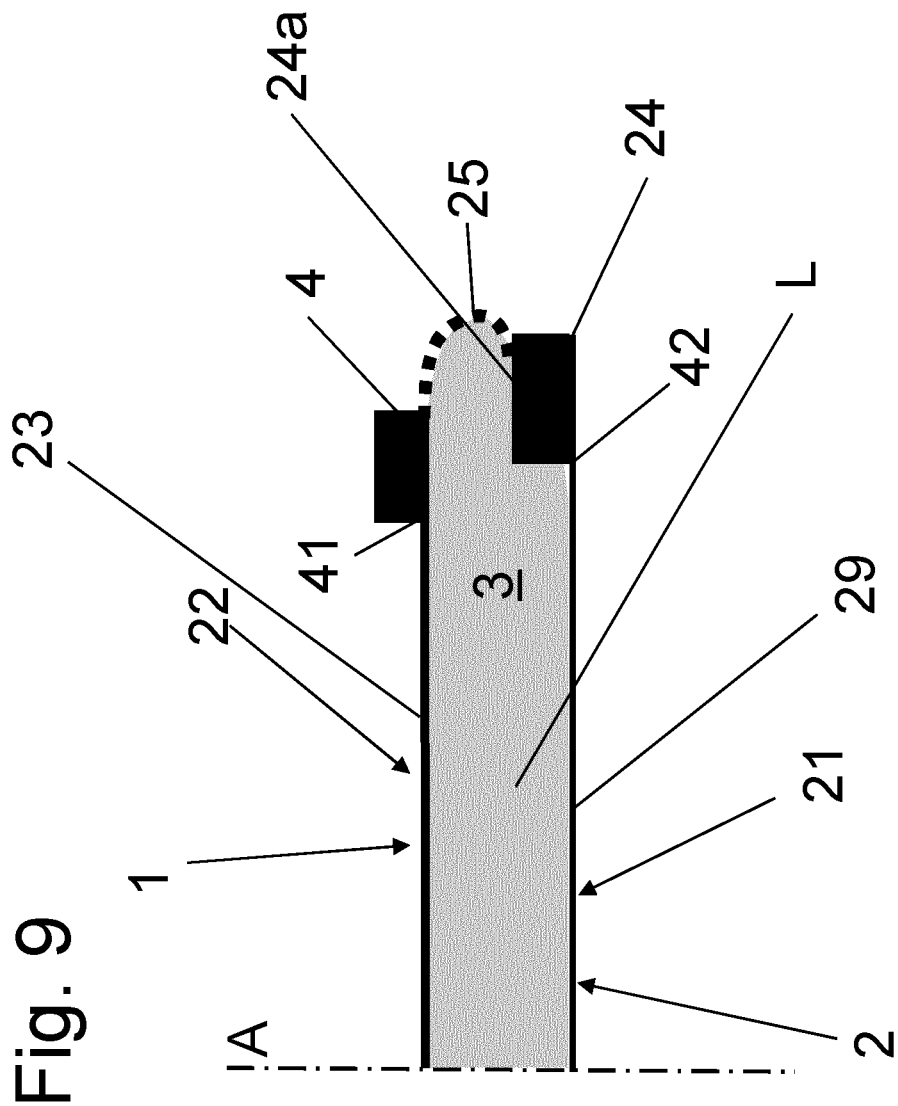
FIG. 9 shows a modification of the embodiment shown in FIG. 8, wherein here the membrane connected to the deformable lens shaping element is formed as a shell.

Furthermore, according to the embodiment shown in FIG. 9, the membrane 22 can be a shell (e.g. thin member formed e.g. out of a glass, plastic material or polymer and comprising e.g. a thickness in the range from 10 μm to 200 μm) which is characterized in that it can also have significant out of plane forces. This means that a pure cylindrical lens (no power in its reference axis) can be achieved without a pressure differential across the shell 22. Further, the spherical power can (almost) exclusively be determined by the shape of further membrane 21 (given E1>>E2, wherein E1 and E2 corresponds to Young's modulus, respectively).

Figure 10:
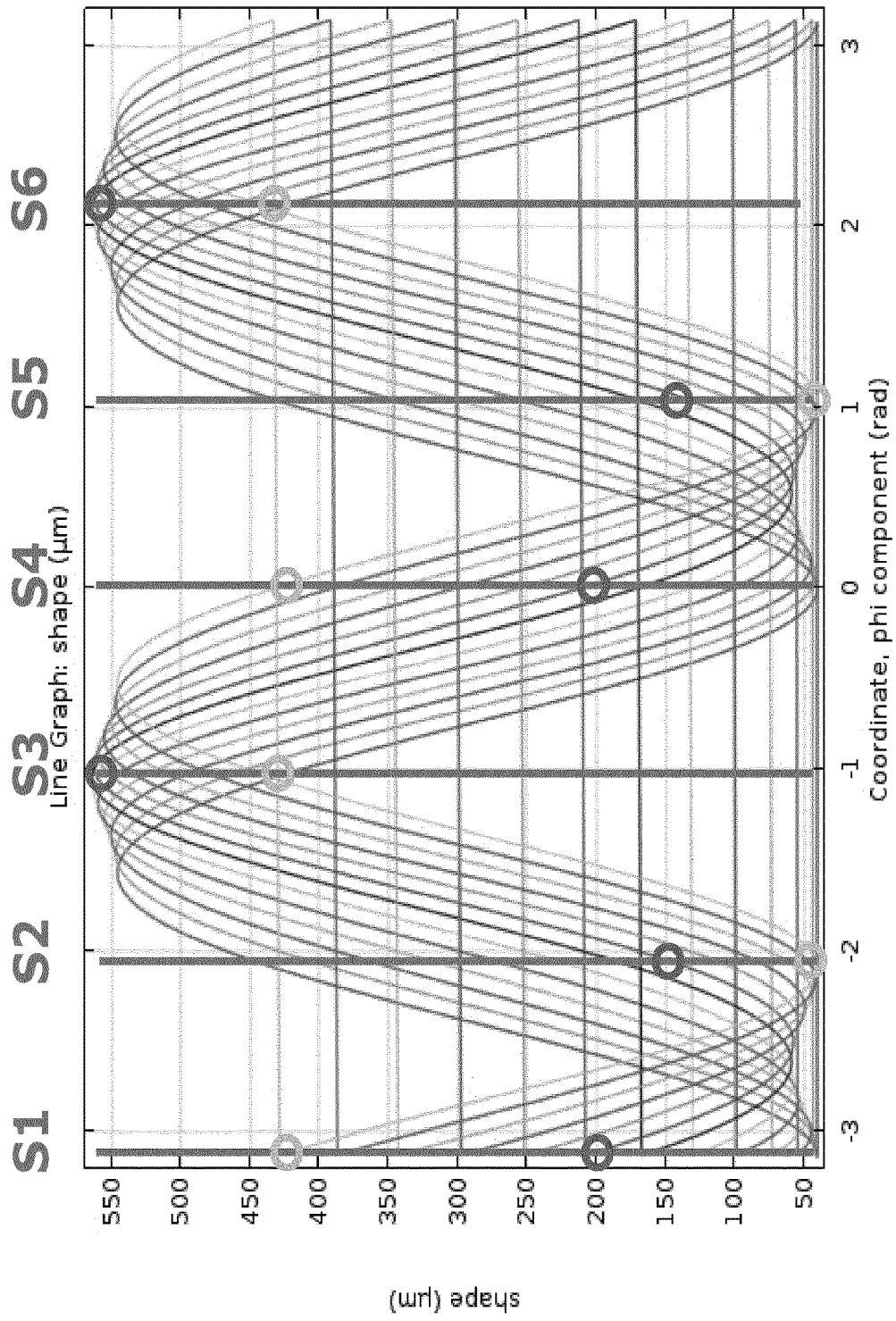
FIG. 10 shows that the cylindrical power of the optical device can be adjusted by acting on a finite number of points of the lens shaping element with a finite number of actuators, here six points and corresponding actuators.

Now, as demonstrated in FIG. 10 it has been surprisingly found out, that the cylindrical power can be adjusted by acting on a finite number of selected points S1, . . . of the lens shaping element 4. Thus, precise control of the cylindrical power can be achieved with a relatively small number of e.g. linear actuators.

Particularly, as depicted in FIG. 10 for two different cylinder angles, the desired deformation of the (ring shaped) lens shaping element 4 (for any cylinder angle) can be achieved by e.g. displacing at least five points, wherein here, as an example six points S1, . . . , S6 are used that are preferably equally spaced on the lens shaping element 4 along the periphery 40 of the element 4.

Particularly, the displacements for liquid pressure (spherical power) and element tilt (sphere and prism) can be advantageously superimposed. Thus, merely six point displacements along the optical axis A are sufficient for full control of sphere, cylinder and prism.

Particularly, in the different embodiments depicted in FIGS. 11 to 14, the optical device 1 comprises an actuator system 30 that is configured to bend the deformable lens shaping element 4 out of the plane P in order to adjust the cylindrical power using only this rather small number of point displacements.

Figure 11:
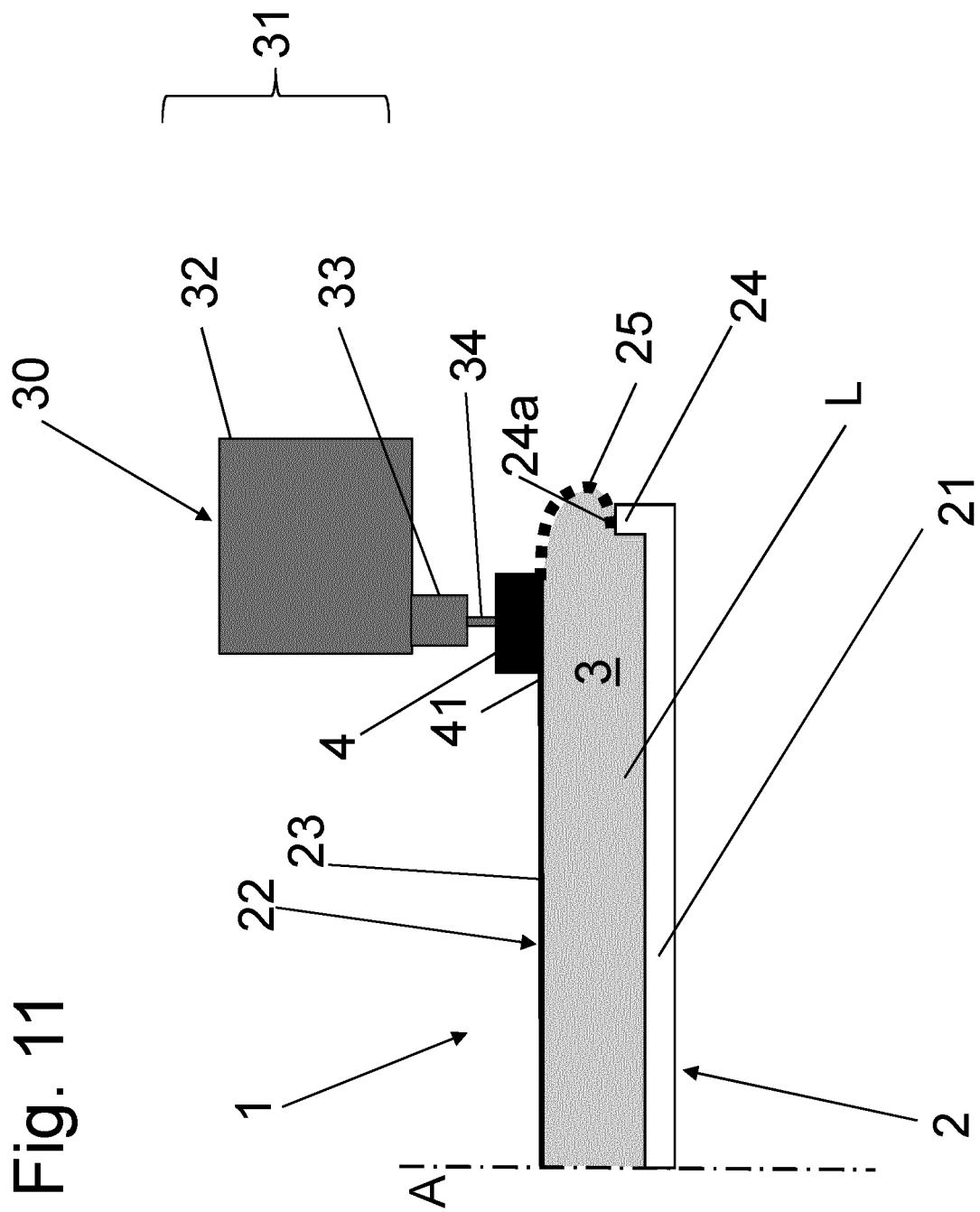
FIG. 11 shows a schematical cross sectional view of an embodiment of an optical device according to the present invention comprising a plurality of actuators comprised by an actuator system, wherein each actuator is configured to act on an associated point of the lens shaping element in push-pull manner.

Particularly, as shown in FIG. 11 the actuator system 30 can comprise individual actuators 31, wherein each actuator 31 is configured to displace one of the points S1, . . . , S6 to bend the deformable lens shaping element 4 out of the plane P in order to adjust the cylindrical power, and particularly also the other powers (sphere and prism).

Particularly, the respective actuator 31 may comprise a stator 32 and a mover 33 that is movable along the optical axis A by means of the actuator 31 and is coupled via a compliant coupling 34 to the respective point S1, . . . , S6 of the lens shaping element 4. As shown in FIG. 11, the respective actuator 31 can be a linear push-pull actuator 31 that can displace the respective point S1, . . . , S6 in opposite directions along the optical axis A/vertical axis A.

Figure 12:
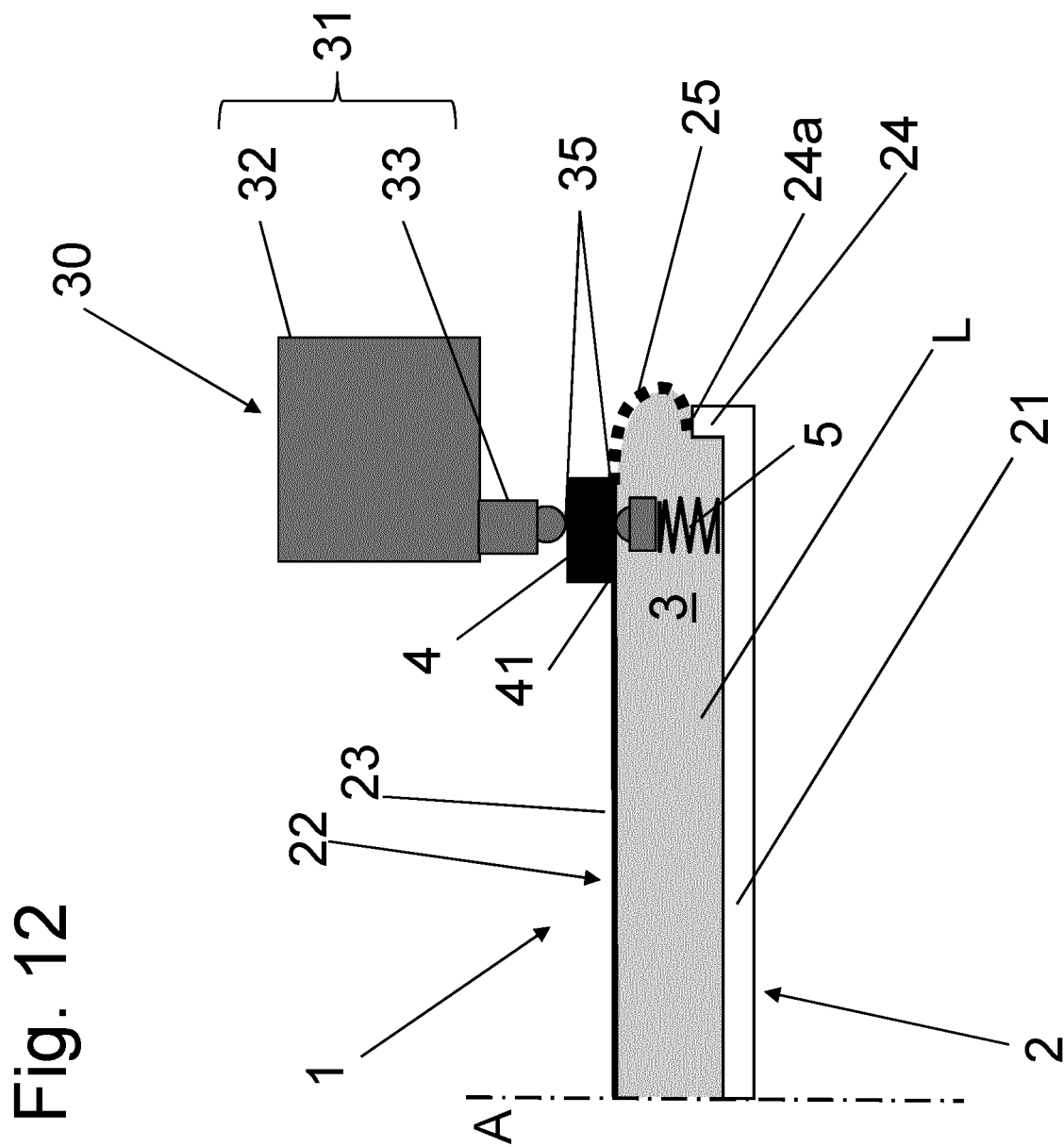
FIG. 12 shows a schematical cross sectional view of a modification of the embodiment shown in FIG. 11, wherein here the respective actuator is configured to push against the associated lens shaping element point while a restoring force is provided by spring elements (e.g. coil springs) that are arranged in the internal space of the container.
Figure 13:
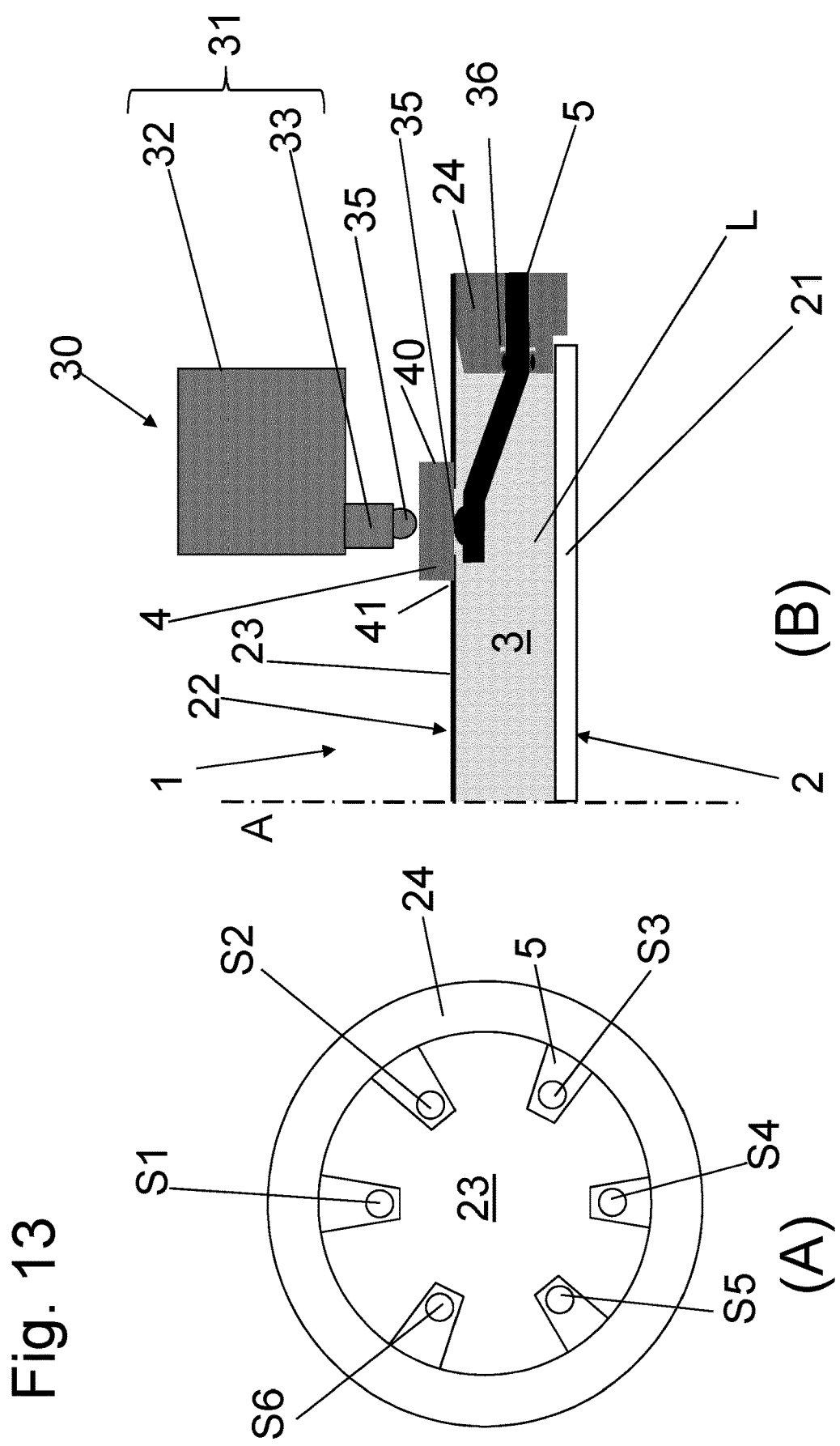
FIG. 13 shows a modification of the embodiment shown in FIG. 12, wherein here leaf springs are employed instead of coil springs. Particularly, (A) shows a schematic top view indicating the position of the individual points, while (B) shows a schematical cross sectional view of the optical device.
Figure 14:
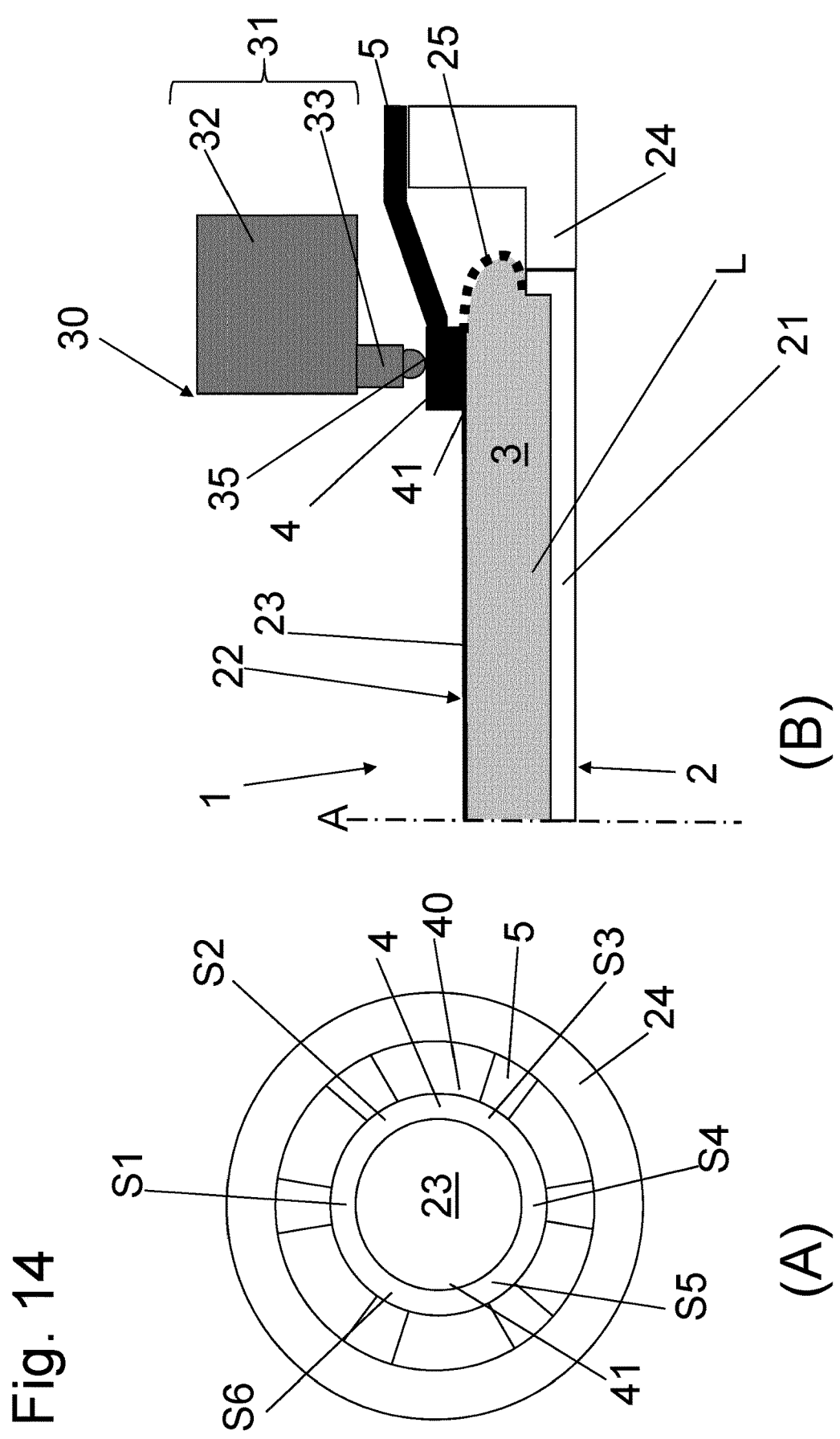
FIG. 14 shows a modification of the embodiment shown in FIG. 13, wherein here the leaf springs are arranged outside the internal space of the container of the optical device. Also here, (A) shows a schematic top view of the device whereas (B) shows a schematical cross sectional view.

Alternatively, the respective actuator 31 can be configured to push against the respective point S1, . . . , S6, wherein a restoring force is provided by an associated spring element 5 as depicted in the embodiments of FIGS. 12, 13 and 14. Also here, the respective actuator 31 can be used to also adjust the spherical and/or prismatic power.

Particularly, according to FIG. 12, the respective spring element 5 can be a coil spring 5. Further, the respective spring element 5 can be arranged in the internal space 3 (i.e. is immersed in the liquid L) and is supported on the bottom 21 of the container 2. Particularly, the lens shaping element 4 is coupled via a point contact 35 to the respective mover 33 and via an opposing point contact 35 to the respective spring element 5.

In contrast to FIG. 12, the respective spring element 5 can also be formed by a leaf spring 5 which can be supported on the lateral wall 24 of the container 2 instead. As shown in FIG. 13 (A), the respective leaf spring 5 can extend radially inwards from the lateral wall 24 and may be mounted to the lateral wall 24 via a seal 36 to avoid leakage of the container 2 (cf. FIG. 13 (B)).

Furthermore, according to FIG. 14, the respective leaf spring 5 can also be supported on the lateral wall 24 of the container 2 outside the internal space 3 as shown in FIGS. 14 (A) and 14 (B) and may extend radially inwards to connect with the lens shaping element 4. Particularly, in the embodiment shown in FIG. 14, the lens shaping element 4 and the springs 5 can be integrally connected to one another and may form a single unit.

Figure 15:
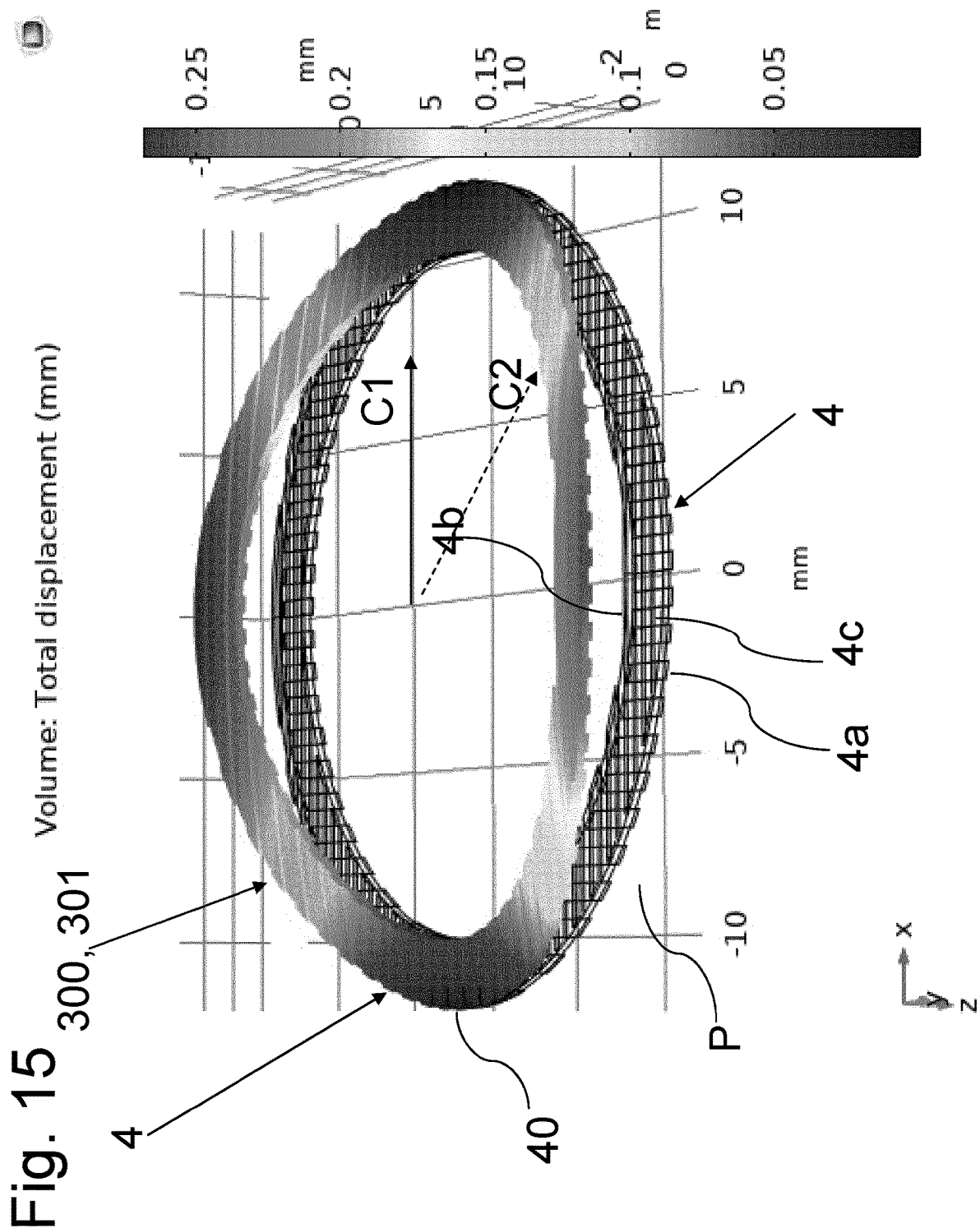
FIG. 15 shows a further embodiment of an actuator for bending the lens shaping element out of plane, wherein here the actuator is a bending actuator.
Figure 16:
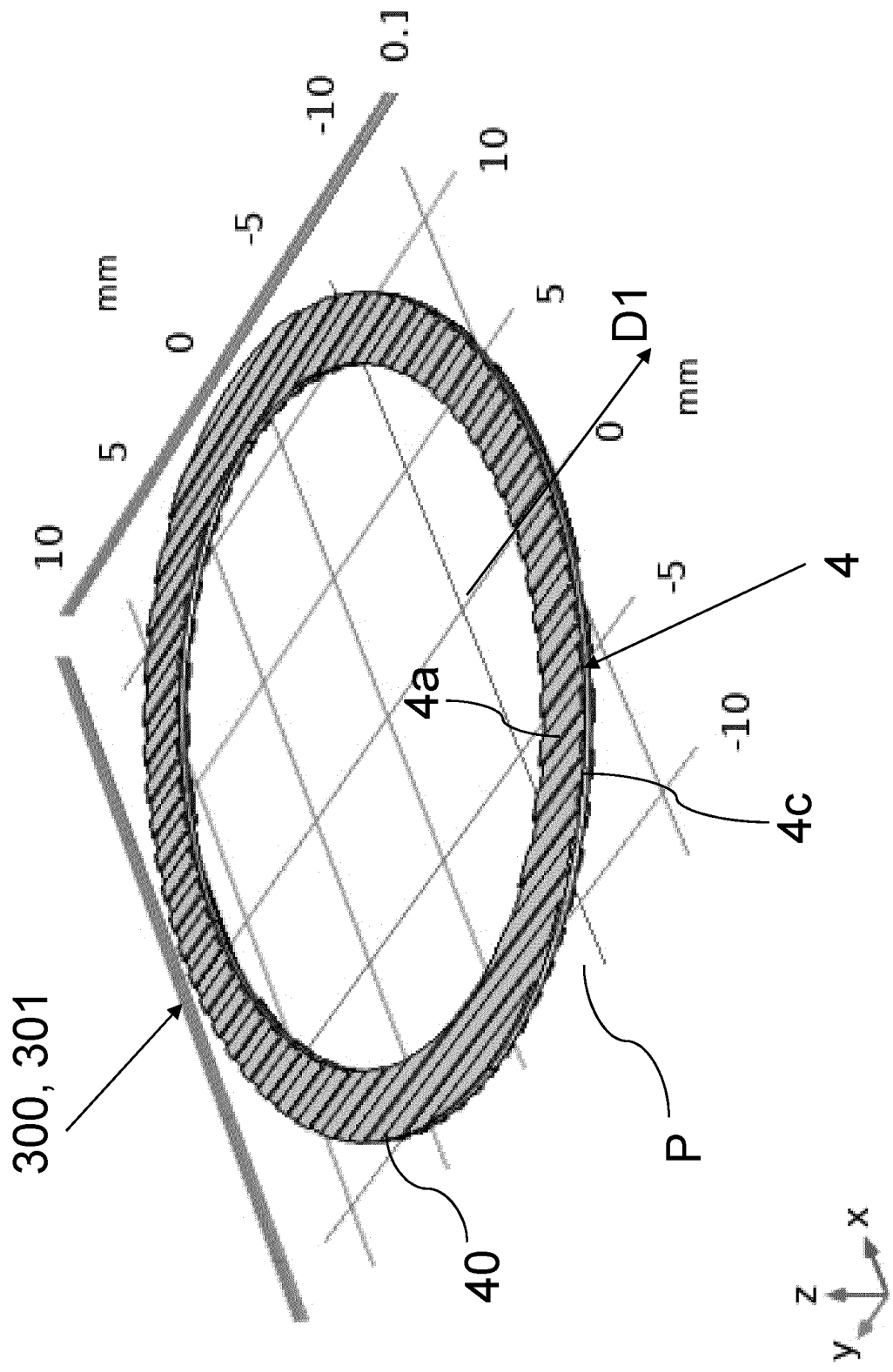
FIG. 16 shows a perspective top view of the bending actuator of FIG. 15.
Figure 17:
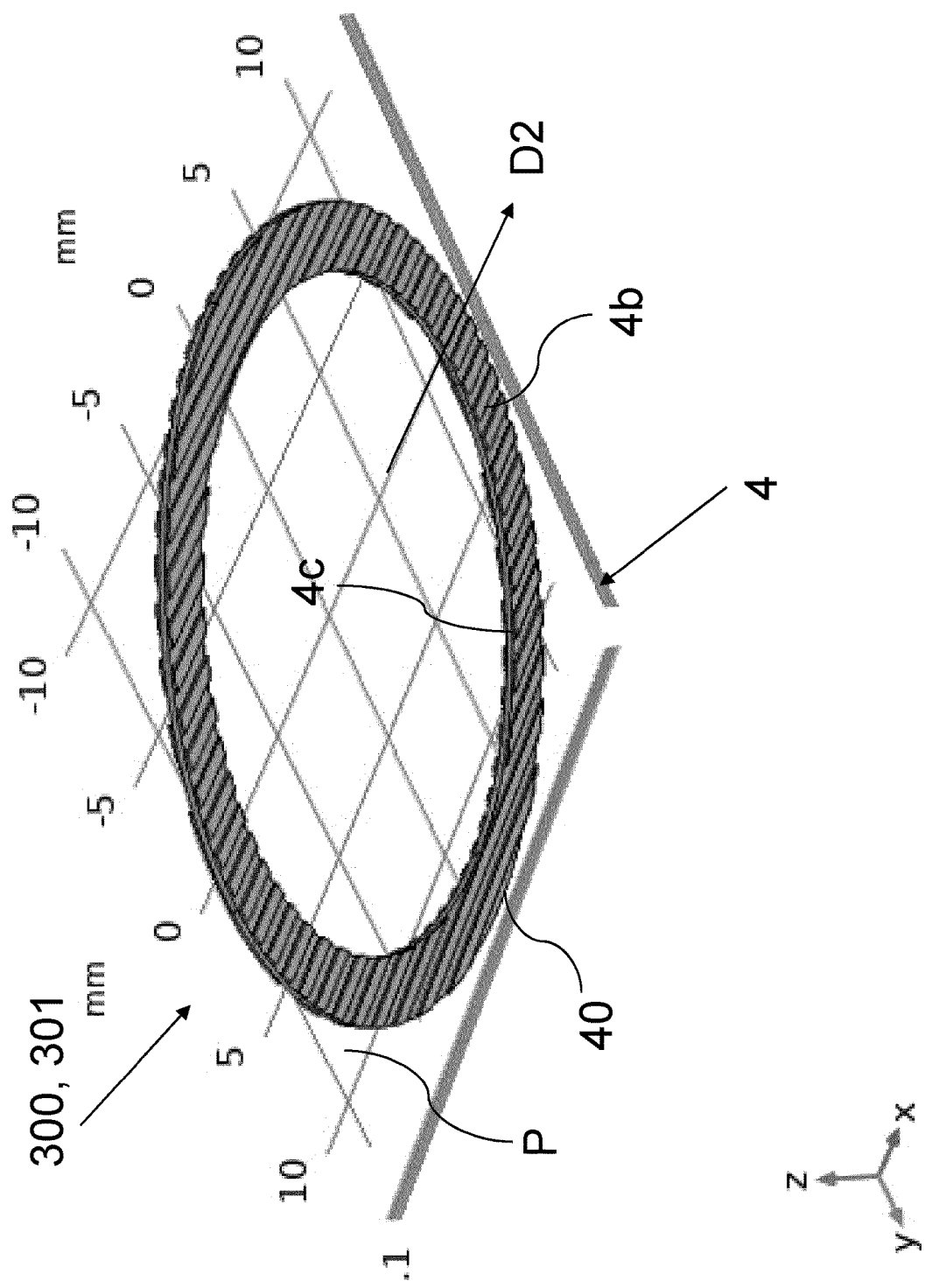
FIG. 17 shows a perspective bottom view of the bending actuator of FIG. 15.

FIG. 15 shows in conjunction with FIGS. 16 and 17 yet another embodiment of an actuator 300 that may be used in conjunction with other actuators of an actuator system or alone to adjust the cylindrical power of the optical device 1.

According to FIGS. 15 to 17, this actuator 300 is a bending (e.g. bimorph) actuator, that comprises an annular passive layer 4c arranged between a first and second annular active layer 4a, 4b, wherein said layers 4a, 4b, 4c are comprised by the lens shaping element 4 or may even form the lens shaping element 4, and wherein the first active layer 4a is configured to anisotropically expand or contract in a first direction D1, and wherein the second active layer 4b is configured to anisotropically expand or contract in a second direction D2 being orthogonal to the first direction D1 to bend the lens shaping element 4 out of said plane P so that the lens shaping element 4 defines a cylindrical surface parallel to a cylinder reference axis C1 (cf. FIG. 15).

Expansion or contraction of the active layers 4a, 4b may be achieved as described above (e.g. by means of an electrical field in case the active layers comprise a piezoelectric material)

However, the bimorph actuator 300 depicted in FIGS. 15 to 17 might only allow to tune the cylindrical power of one given reference axis. In that case two such deformable lens shaping elements 4, 24/actuators 300, 301 are required, whose cylinder reference axes C1, C2 form an angle of 45° as shown in FIG. 15.

Figure 18:
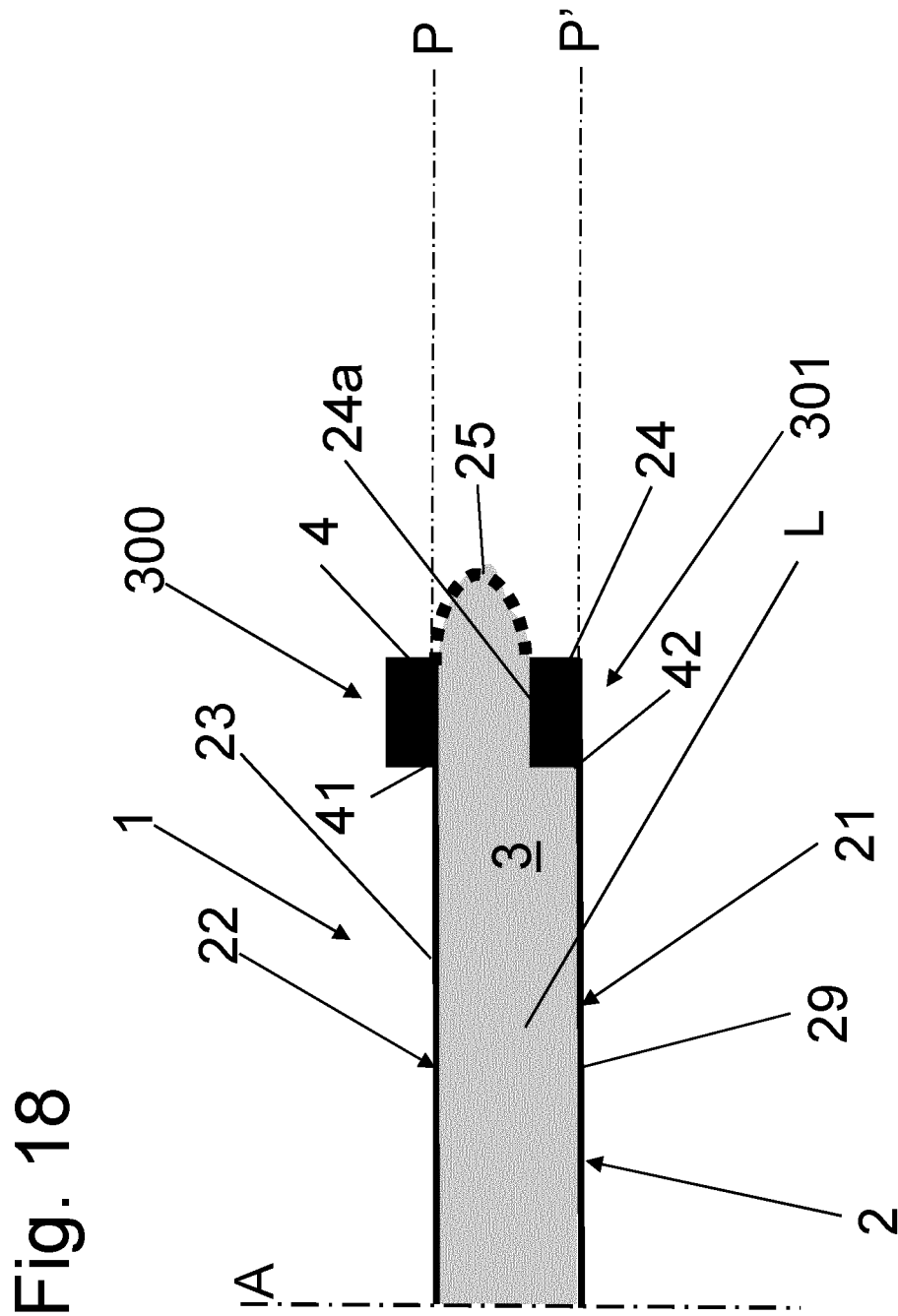
FIG. 18 indicates how two opposing bending actuators can be used to allow tuning the cylindrical power for multiple cylinder reference axes.

Such a configuration comprising two actuators 300, 301 is schematically illustrated in FIG. 18. Here, the optical device 1 is configured as described in conjunction with FIG. 8, but the further lens shaping element 24 is now also deformable (like the lens shaping element 4), wherein in a non-deformed state the further lens shaping element 24 defines a further plane P', wherein for adapting the cylindrical power of the optical device 1, the further lens shaping element 24, like the lens shaping element 4, is configured to be bent out of said further plane P' so that the further lens shaping element 24 also defines a cylindrical surface or generates a cylindrical power. In order to achieve a variable reference axis, the two actuators 300, 301 can be rotated with respect to one another by said 45° as shown in FIG. 15.

Figure 19:
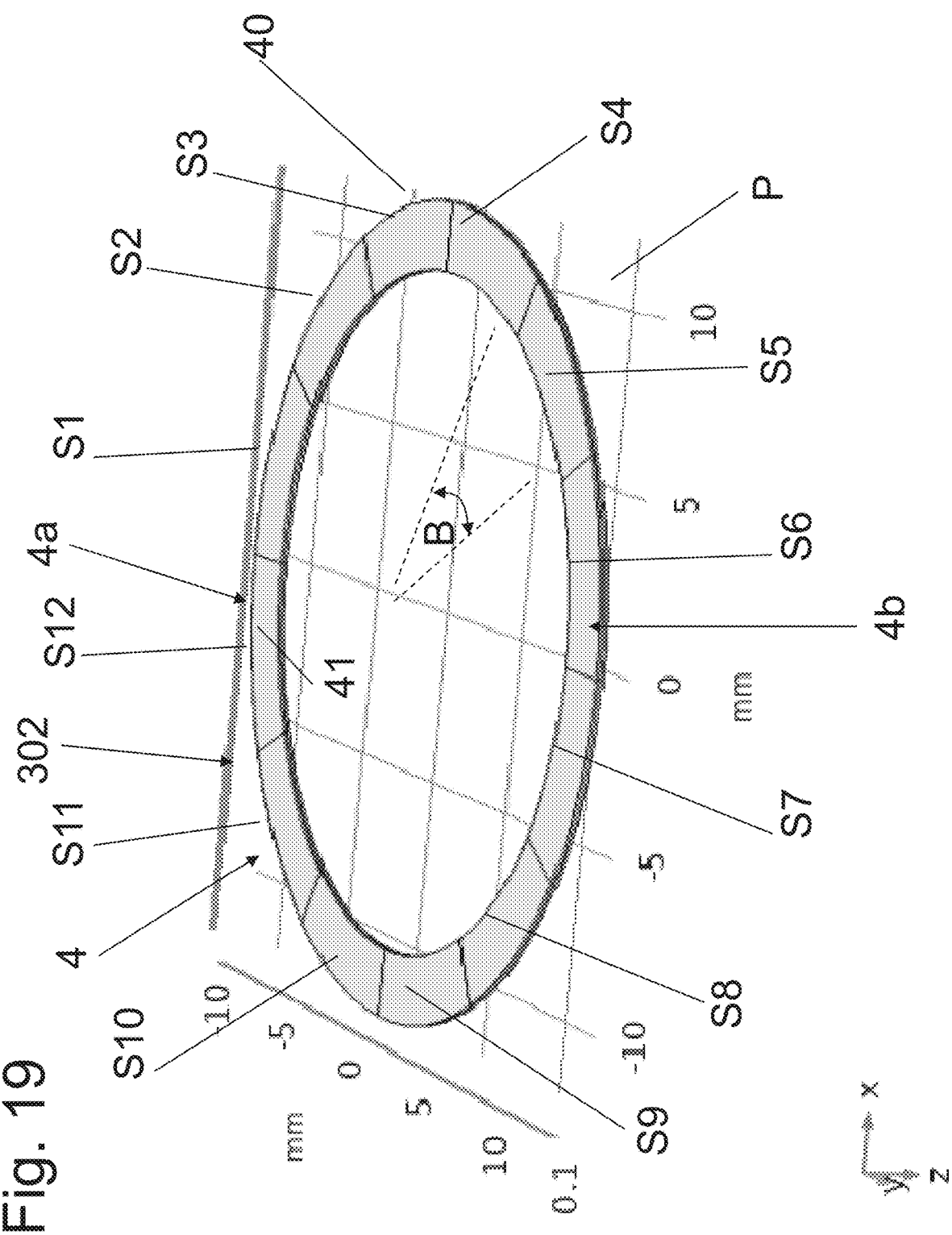
FIG. 19 shows a further bending actuator for bending the lens shaping element out of plane regarding different cylinder reference axes, wherein the bending actuator comprises adjacent segments of an active layer that can expand/contract (e.g. isotropically)
Figure 20:
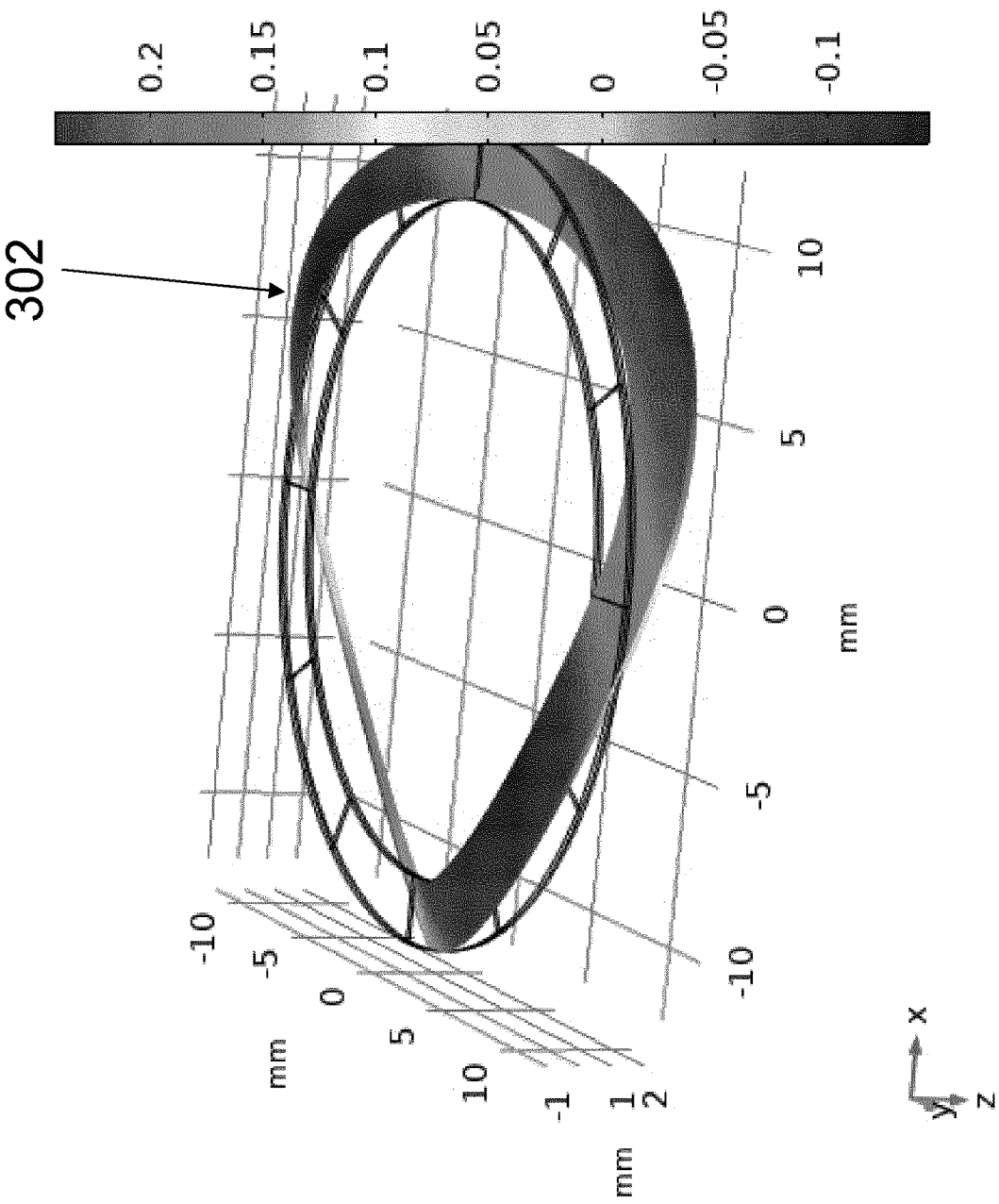
FIG. 20 shows a state in which the lens shaping element is bent out of plane using the actuator shown in FIG. 19.
Figure 21:
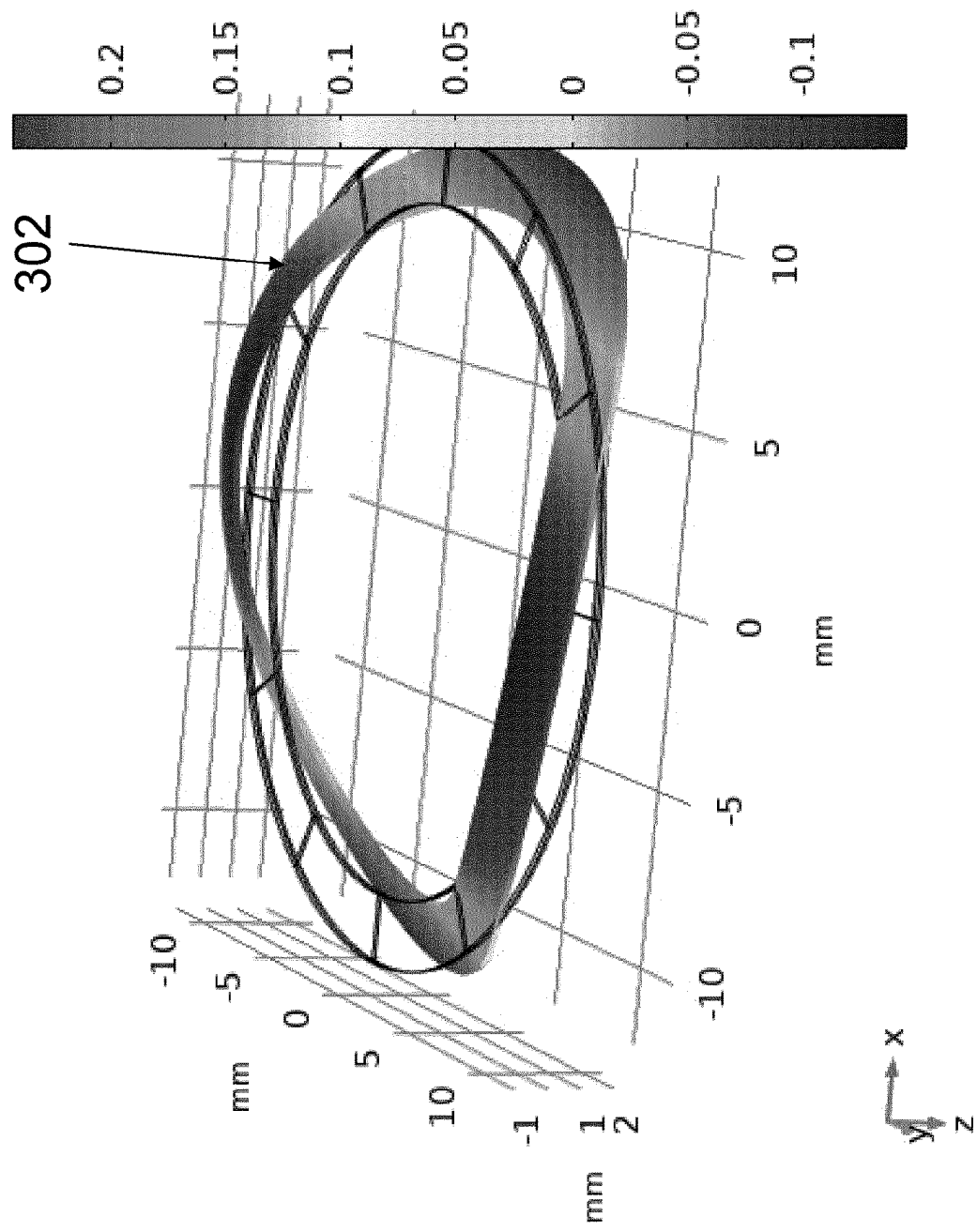
FIG. 21 shows a further state (with a different cylinder reference axis) in which the lens shaping element is bent out of plane using the actuator shown in FIG. 19.

FIG. 19 shows in conjunction with FIGS. 20 and 21 a further embodiment of an actuator 302 of an optical device 1 according to the present invention, wherein here the actuator 302 is a bending (e.g. bimorph) actuator 300 that comprises an annular passive layer 4b and an annular active layer 4a, wherein said layers 4a, 4b are comprised by the lens shaping element 4 or even form the lens shaping element 4, and wherein the active layer 4a comprises adjacent segments S1, . . . , S12 arranged side by side in a circumferential direction of the active layer 4a that are configured to be selectively activated to contract or expand isotropically or anistropically. This allows a variable out-of-plane bending of the lens shaping element 4 as shown in FIGS. 20 and 21.

Particularly, the active layer 4a may comprise twelve segments S1, . . . , S12, wherein each segment comprises a length in the circumferential direction that corresponds to a center angle B of the annular active layer 4a of 30°.

Also here, expansion or contraction of the respective segment S1, . . . , S12 may be achieved as described above (e.g. by means of an electrical field in case the segments comprise a piezo-electric material).

Figure 22:
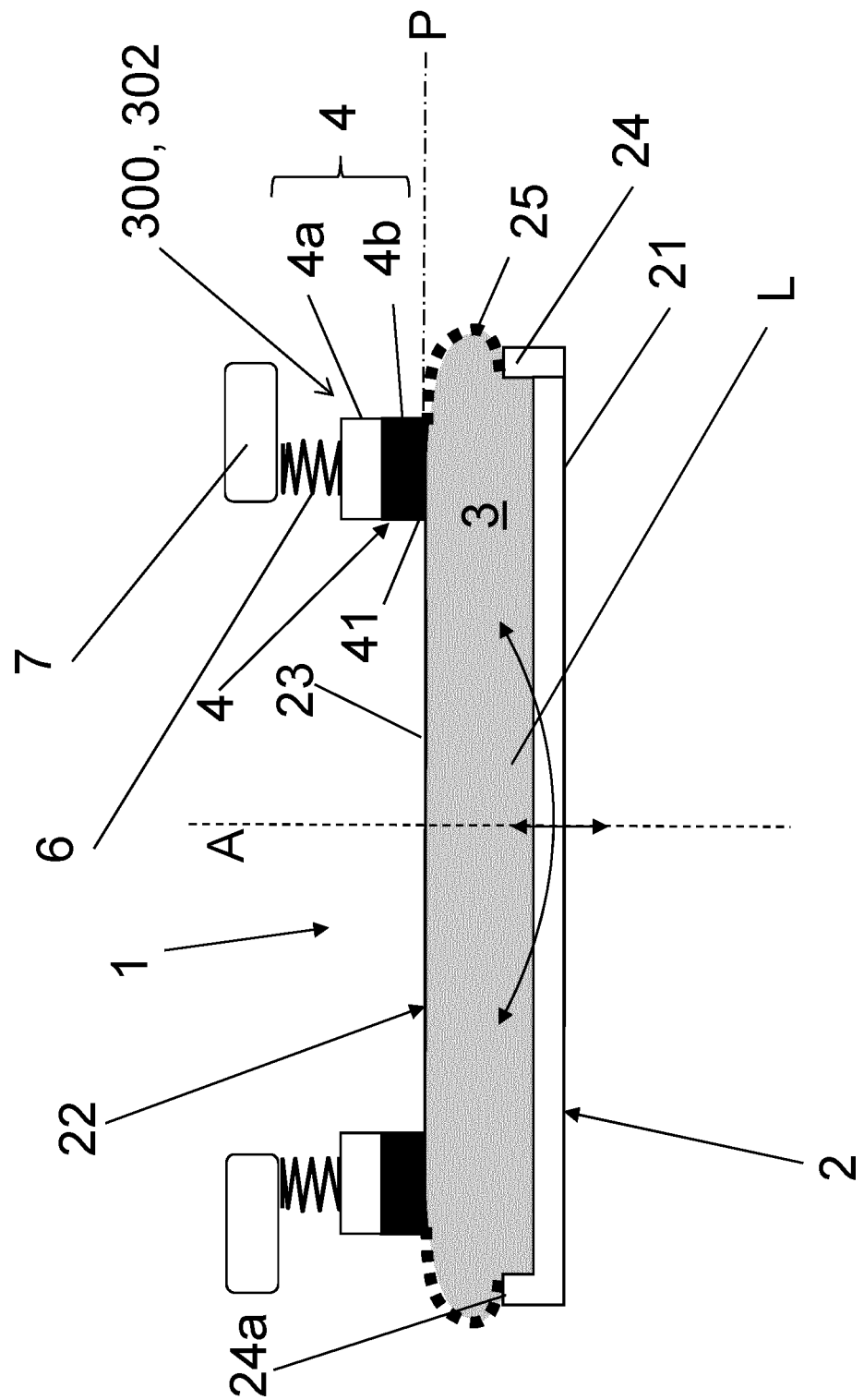
FIG. 22 shows an embodiment of an optical device according to the present invention that comprises e.g. the actuator shown in FIG. 20, wherein the lens shaping element/actuator is elastically coupled to a holding structure, and wherein the bottom of the container is configured to be tilted or moved axially with respect to the lens shaping element to tune the spherical and the prismatic power.

Particularly, such an actuator 302 can be used in any embodiment according to the present invention. Particularly, FIG. 22 shows an application of such an actuator 302, wherein the lens shaping element 4 that is formed by the actuator 300 is elastically mounted to a holding structure 7 (e.g. a fixed base) of the optical device 1 via an elastic mounting 6.

Using this coupling, the container 2 can be tilted with respect to the optical axis A (e.g. by a suitable further actuator of the actuator system) to adjust the prismatic power of the optical device 1. Furthermore, the container 2 or bottom 21 can be moved along the optical axis A of the optical device 1 with respect to the lens shaping element 4 to adjust the spherical power of the optical device 1.

Figure 23:
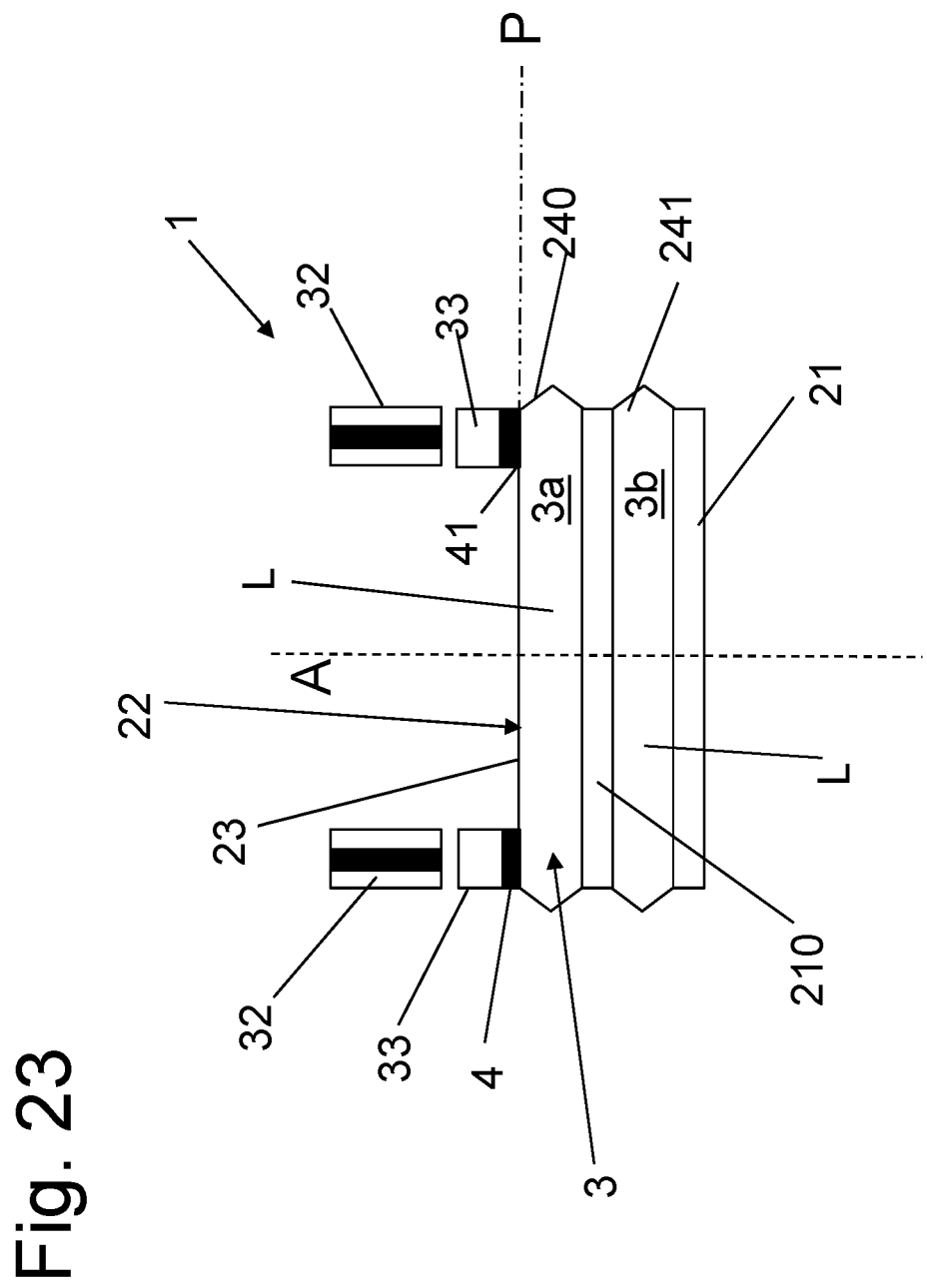
FIG. 23 shows a further embodiment of an optical device according to the present invention that allows bending the lens shaping element to adjust the cylindrical power and to tilt the bottom of the container for tuning the prismatic power.

Furthermore, FIG. 23 shows a further embodiment of the present invention, wherein here, the cylindrical power, and particularly the spherical power, is adjustable by means of individual actuators 31, wherein each actuator 31 comprises e.g. an electromagnet 32 that moves a magnet 33 (mover) coupled to the lens shaping element 4, so that the latter can be bent out of its initial plane P as described above (e.g. by displacing at least five points, particularly six points, of the lens shaping element 4 as describe above). In order to tune the prismatic power, the optical device 1 further comprises a transparent optical element 210 arranged between the membrane 22 and the bottom 21 such that the internal space 3 of the container 2 of the optical device 1 is divided into two separate regions 3a, 3b, wherein each region 3a, 3b is filled with the liquid L and wherein the optical device 1 comprises a flexible first lateral wall 240 that can be formed by a bellows, and a flexible second lateral wall 241, that can also be formed by a bellows, wherein the first lateral wall 240 connects the lens shaping element 4 to the optical element 1, and wherein the second lateral wall 241 connects the optical element to the bottom 21. Thus, the bottom 21 can now be tilted by an actuator of the actuator system with respect to the optical element 210 (e.g. a transparent flat glass or polymer member) in order to adjust the prismatic power of the optical device 1, whereas the actuators 31 can be used to displace the magnets 33 to adjust the cylindrical power and/or the spherical power of the optical device 1.

The invention claimed is:

1. An optical device, comprising:
a container enclosing an internal space of the container, wherein the internal space is filled with a transparent liquid, and wherein the container comprises a transparent bottom and a transparent and elastically deformable membrane opposing said bottom such that the liquid is arranged between the membrane and the bottom,
a deformable annular lens shaping element connected to the membrane so that a circumferential edge of the deformable annular lens shaping element defines a central area of the membrane so that light can pass through the container via the central area and the bottom, wherein in a non-deformed state said edge lies in a plane, and
an adjustable spherical power and an adjustable cylindrical power, wherein for adapting the cylindrical power of the optical device, the deformable annular lens shaping element is configured to be bent out of said plane,
wherein the optical device comprises an actuator system that is configured to bend the deformable annular lens shaping element out of the plane in order to adjust the cylindrical power, the actuator system is configured to displace a plurality of points of the deformable annular lens shaping element along an optical axis of the optical device to bend the deformable annular lens shaping element out of the plane in order to adjust the cylindrical power,
the actuator system comprises a plurality of actuators, wherein each actuator is configured to displace one of the points, and
each actuator comprises a mover that is movable towards the deformable annular lens shaping element along the optical axis of the optical device by means of the actuator, wherein each mover is configured to push against the associated point of the deformable annular lens shaping element via a point contact.

2. The optical device according to claim 1, wherein for adapting the cylindrical power of the optical device, the deformable annular lens shaping element is configured to be bent out of said plane so that said edge of the deformable annular lens shaping element coincides with a cylindrical surface.

3. The optical device according to claim 1, wherein the optical device comprises an adjustable prismatic power.

4. The optical device according to claim 1, wherein the bottom forms an elastically deformable second membrane, and wherein the optical device comprises an annular second lens shaping element connected to the elastically deformable second membrane so that a circumferential edge of the annular second lens shaping element defines a central area of the elastically deformable second membrane.

5. The optical device according to claim 4, wherein the annular second lens shaping element is a deformable annular second lens shaping element, wherein in a non-deformed state said edge of the deformable annular second lens shaping element defines a further plane, wherein for adapting the cylindrical power of the optical device, the deformable annular second lens shaping element is configured to be bent out of said further plane.

6. The optical device according to claim 4, wherein the annular second lens shaping element is rigid.

7. The optical device according to claim 4, wherein the transparent and elastically deformable membrane forms a shell having a nondimensional tension parameter k smaller than 5, wherein
the nondimensional tension parameter k is defined as $$k = \sqrt{\frac{N_0 a^2}{D}}$$

where $N_0$ is the initial in plane radial tension load, a is the radius of the circular membrane and D is the bending stiffness.

8. The optical device according to claim 4, wherein the actuator system is configured to tilt the lens shaping elements with respect to one another to adjust the prismatic power of the optical device.

9. The optical device according to claim 1, wherein the optical device comprises a transparent optical element arranged between the membrane and the bottom such that the internal space is divided into two separate regions, and wherein the optical device comprises a flexible first lateral wall and a flexible second lateral wall, wherein the first lateral wall connects the lens shaping element to the optical element, and wherein the second lateral wall connects the optical element to the bottom.

10. The optical device according to claim 1, wherein said points are distributed along the periphery of the deformable annular lens shaping element.

11. The optical device according to claim 1, wherein said plurality of points (S1, .... S6) comprises at least five points or; six points.

12. The optical device according to claim 1, wherein said points are equidistantly spaced along the periphery of the deformable annular lens shaping element.

13. The optical device according to claim 1, wherein the actuator system is configured to displace the points along the optical axis of the optical device to adjust the spherical power of the optical device.

14. The optical device according to claim 1, wherein the actuator system is configured to displace points of the deformable annular lens shaping element such that the lens shaping element is tilted with respect to the optical axis of the optical device to adjust the prismatic power of the optical device.

15. The optical device according to claim 1, wherein each actuator comprises a mover that is movable towards or away from the deformable annular lens shaping element along the optical axis of the optical device by means of the actuator, wherein each mover is configured to push against or pull on an associated point of the deformable annular lens shaping element, and wherein each actuator comprises a spring element configured to exert a restoring force on the associated point of the deformable annular lens shaping element, wherein the deformable annular lens shaping element is coupled via a point contact to the respective mover and ene of: coupled via an opposing point contact to the respective spring element, or integrally formed with the respective spring element.

16. The optical device according to claim 15, wherein the respective spring element is supported on the bottom of the container, or the respective spring element is supported on a lateral wall.

17. The optical device according to claim 15, wherein the respective spring element is a coil spring or a leaf spring.

18. The optical device according to claim 15, wherein the respective spring element is arranged in the internal space and immersed in the liquid, or the respective spring element is arranged outside the internal space of the container.

\* \* \* \* \*